[19] United States Patent
Murashiro et al.

[11] Patent Number: 5,427,714
[45] Date of Patent: Jun. 27, 1995

[54] FERROELECTRIC LIQUID CRYSTAL COMPOSITION

[75] Inventors: Katsuyuki Murashiro, Ichiharashi; Makoto Kikuchi, Kisarazushi; Kanetsugu Terashima, Ichiharashi, all of Japan

[73] Assignee: Chisso Corporation, Osaka, Japan

[21] Appl. No.: 96,848

[22] Filed: Jul. 26, 1993

Related U.S. Application Data

[63] Continuation of Ser. No. 692,228, Apr. 26, 1991, abandoned.

[30] Foreign Application Priority Data

May 23, 1990 [JP] Japan .................. 2-133119
Nov. 30, 1990 [JP] Japan .................. 2-334432

[51] Int. Cl.$^6$ .......................... C09K 19/34; G02F 1/13
[52] U.S. Cl. ............................ 252/299.61; 359/103
[58] Field of Search ................ 252/299.61; 359/103

[56] References Cited

U.S. PATENT DOCUMENTS

| | | | |
|---|---|---|---|
| 4,882,083 | 11/1989 | Terashima et al. | 252/299.61 |
| 4,882,086 | 11/1989 | Terashima et al. | 252/299.61 |
| 4,892,393 | 1/1990 | Terashima et al. | 350/350 S |
| 4,952,335 | 8/1990 | Furukawa et al. | 252/299.61 |
| 4,973,426 | 11/1990 | Ohno et al. | 252/299.66 |
| 4,985,172 | 1/1991 | Wingen et al. | 252/299.67 |
| 5,021,190 | 6/1991 | Kikuchi et al. | 252/299.61 |
| 5,047,172 | 9/1991 | Saito et al. | 252/299.61 |
| 5,064,568 | 11/1991 | Terashima et al. | 252/299.61 |
| 5,080,827 | 1/1992 | Miyazawa et al. | 252/299.66 |
| 5,116,529 | 5/1992 | Terashima et al. | 252/299.61 |
| 5,149,461 | 9/1992 | Terashima et al. | 252/299.61 |
| 5,188,761 | 2/1993 | Terashima et al. | 252/299.61 |
| 5,190,691 | 3/1993 | Kikuchi et al. | 252/299.61 |
| 5,198,150 | 3/1993 | Takeshita et al. | 252/299.61 |
| 5,240,638 | 8/1993 | Kikuchi et al. | 252/299.61 |
| 5,294,367 | 3/1994 | Terashima et al. | 252/299.61 |

FOREIGN PATENT DOCUMENTS 0328330 8/1989 European Pat. Off. .
145683 6/1990 Japan .
2659864 10/1990 Japan .

*Primary Examiner*—Cynthia Harris
*Attorney, Agent, or Firm*—Leydig, Voit & Mayer

[57] ABSTRACT

A ferroelectric liquid crystal composition having a SC* phase and a light-switching element using the composition are provided, which composition comprises the following components, A, B and C, each in a specified proportion: Component A has the formula $$R^1-\left(A\right)_l-\left(B\right)_m-\left\langle\begin{array}{c}N\\\|\\N\end{array}\right\rangle-\left(\bigcirc\right)_n-R^2 \quad (A)$$

wherein $-\left(A\right)-$ and $-\left(B\right)-$ are $-\left(\bigcirc^X\right)-$ or $-\left(\bullet\right)-,$ $R^1$ and $R^2$ are same or different linear or branched alkyl, alkoxy or alkanoyloxy of 1–18C, X is H, halogen or CN, l, m and n are 0 or 1 and (l+m+n) is 1 or 2, and has smectic C phase;

Component B has the formula $$R^3-\left(C\right)-\left(D\right)-\left(E\right)_{\overline{k}}-O-CH_2-\overset{CH_3}{\underset{*}{CH}}-O\overset{O}{\overset{\|}{C}}-\overset{CH_3}{\underset{*}{CH}}-R^4 \quad (B)$$

wherein (Abstract continued on next page.)

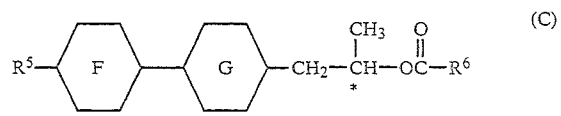 (C)

wherein

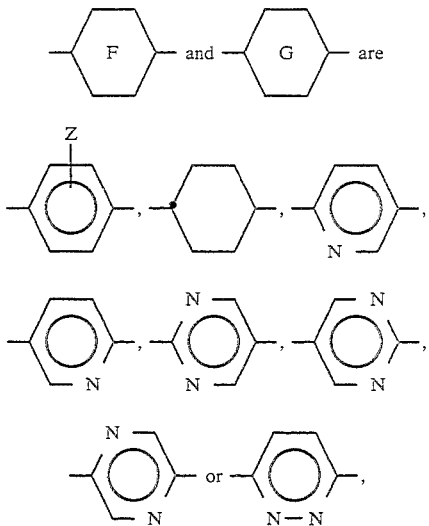 and 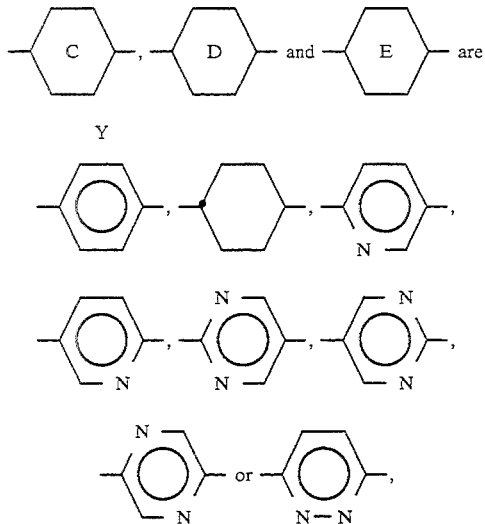 are

Y is H, halogen or CN, k is 0 or 1, $R^3$ is linear or branched alkyl or alkoxy of 1–18C, and * is asymmetric C, and consists of optically active compounds having the same senses of Ps in SC* phase induced when dissolved in smectic C liquid crystal, to one another; and Component C has the formula Z is H, halogen or CN, $R^5$ and $R^6$ are same or different linear or branched alkyl or alkoxy of 1–18C $R^4$ is 12–18C alkyl or 1–18C linear or branched alkoxy, and * is asymmetric C, and is an optically active compound having the same sense of Ps in SC* phase induced when dissolved in smectic C liquid crystal as that of the compound of component B.

24 Claims, No Drawings

FERROELECTRIC LIQUID CRYSTAL COMPOSITION

This application is a continuation of application Ser. No. 07/692,228, filed Apr. 26, 1991, now abandoned.

BACKGROUND OF THE INVENTION

1. Field of the Invention

This invention relates to a liquid crystal material as a display material employed utilizing an electrooptical effect. More particularly, it relates to a ferroelectric liquid crystal mixture and a light-switching element using the same.

2. Description of the Related Art

Ferroelectric liquid crystals are materials capable of realizing an incommensurably quick electrooptical response as compared with that of nematic liquid crystals now broadly used as a display material; thus research in the practical use of the ferroelectric liquid crystals has been made. Among chiral smectic liquid crystal phases known to exhibit ferroelectricity, the chiral smectic C phase (hereinafter abbreviated to SC* phase) has been particularly noted.

The display using the chiral smectic C liquid crystal exhibits (1) a quicker electrooptical response than that of a nematic liquid crystal,
(2) memory properties and
(3) a wide viewing angle;

hence it has been expected to use the liquid crystal in practice as a material having a potential high density display. At present, requirements for ferroelectric liquid crystals as a practical display material are as follows:

(1) exhibition of the SC* phase within a broad temperature range including room temperature,
(2) quick electrooptical response, and
(3) superior alignment.

It has been required for the electrooptical response that the response time be 100 μsec or shorter at an impressed voltage of 5 V/μm. Such response properties have been regarded as necessary for highly-multiplexable liquid crystal display elements provided with 640×400 lines or more.

As for the method of aligning ferroelectric liquid crystals, three methods referred to as the shearing method, temperature gradient method and surface treatment method have now been attempted. Among these methods, alignment of liquid crystal molecules according to the surface treatment is most preferred in the aspect of commercial production of liquid crystal display elements. In order to apply the surface treatment method now used for aligning nematic liquid crystals also to ferroelectric smectic C liquid crystals, it has been required that the ferroelectric smectic C liquid crystal materials exhibit two liquid crystal phases of the cholesteric phase (hereinafter abbreviated to N* phase) and the smectic A phase (hereinafter abbreviated to SA phase) besides SC* phase, and also that the liquid crystal materials take a phase transition series starting from isotropic liquid phase (hereinafter abbreviated to Iso phase), via the N* phase and the SA phase to the SC* phase (for example, see Japanese patent application laid-open No. Sho 61-250086). An aligning technique according to the surface treatment method of the ferroelectric smectic C liquid crystals deficient in the N* phase or the SA phase has not yet been established.

Japanese patent application laid-open No. Sho 61-291679 illustrates a ferroelectric liquid crystal mixture consisting of a smectic C liquid crystalline pyrimidine compound and a liquid crystal having a SC* phase. Further, the pamphlet of PCT International laid-open WO 86/06401 alike illustrates a ferroelectric liquid crystal mixture having a component of a smectic C liquid crystalline pyrimidine compound. However, these ferroelectric liquid crystals have a response time as long as 300 to 600 μsec; hence they cannot be regarded as practical.

Japanese patent application laid-open No. Sho 63-301290 illustrates a ferroelectric liquid crystal mixture comprising a smectic C liquid crystalline pyrimidine compound and an optically active compound of the formula (B-V) in Example 5. This mixture has superior response properties, but has no N* phase; hence it has a drawback that alignment according to the surface treatment method is impossible.

SUMMARY OF THE INVENTION

As described above, it can be said that no practical ferroelectric liquid crystal has yet been obtained.

A first object of the present invention is to provide a ferroelectric liquid crystal composition having a SC* phase within a broad temperature range including room temperature, easily affording a good alignment according to the surface treatment method and having high speed response properties of a response time of 100 μsec or less.

A second object of the present invention is to provide a light-switching element exhibiting a quick electrooptic response within a broad temperature range and having a good alignment.

The first object of the present invention is achieved according to the following item (1). The items (2) to (11) described below show the embodiments of the above invention.

The second object of the present invention is achieved according to the item (12) described below.

(1) A ferroelectric smectic C liquid crystal composition comprising the following three components A, B and C, the mixing proportions of component A, component B and component C being 55 to 91% by weight, 5 to 25% by weight and 4 to 20% by weight, respectively, based upon the total quantity of the three components:

The component A is at least one compound selected from among compounds expressed by the formula

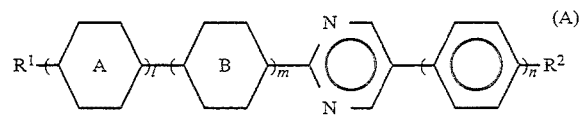

wherein

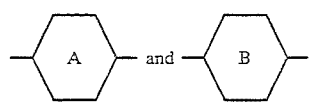

and each independently represent

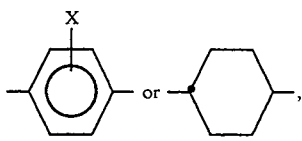

R¹ and R² each represent the same or different linear or branched alkyl group, alkoxy group or alkanoyloxy group each of 1 to 18 carbon atoms, X represents a hydrogen atom, a halogen atom or a cyano group, l, m and n each represent an integer of 0 or 1 and (l+m+n) is 1 or 2, and having a smectic C phase;

the component B is at least one compound selected from among optically active compounds expressed by the formula

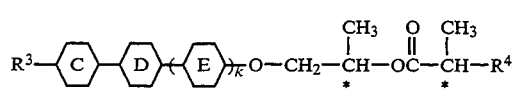 (B)

wherein

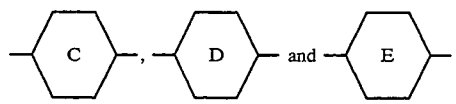

each independently represent

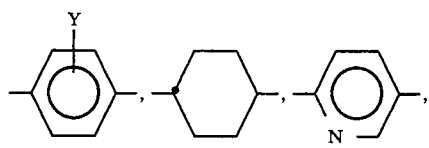

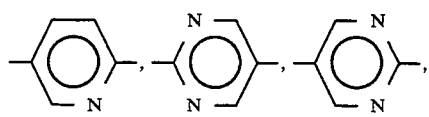

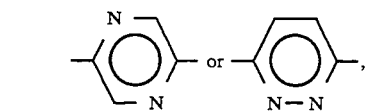

Y represents hydrogen atoms, a hydrogen atom or cyano group, k represents an integer of 0 or 1, $R^3$ represents a a linear or branched alkyl group or alkoxy group each of 1 to 18 carbon atoms, $R^4$ represents an alkyl group of 2 to 18 carbon atoms or a linear or branched alkoxy group of 1 to 18 carbon atoms and the symbol * represents an asymmetric carbon atom, the above-mentioned optically active compounds having to one another the same sense of the spontaneous polarization in a chiral smectic C phase induced when dissolved in a smectic C liquid crystal; and the component C is at least one compound selected from among optically active compounds expressed by the formula

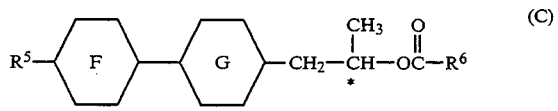 (C)

wherein

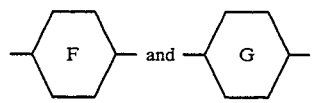

each independently represent

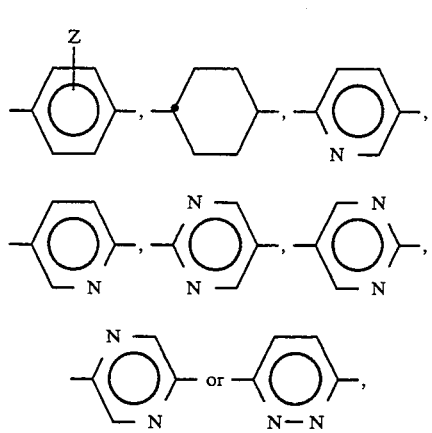

Z represent a hydrogen atom, a halogen atom or cyano group, $R^5$ and $R^6$ each represent the same or different linear or branched alkyl group or alkoxy group each of 1 or 18 carbon atoms and the symbol * represents an asymmetric carbon atom, the above-mentioned optically active compounds having the same sense of the spontaneous polarization in a chiral smectic C phase induced when dissolved in a smetic C liquid crystal, as the sense of the compounds of the component B.

(2) A ferroelectric smectic C liquid crystal composition according to item (1), wherein the component A is at least one compound selected from compounds expressed by the formula

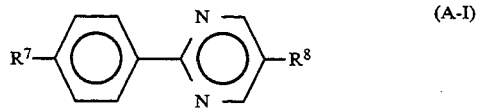 (A-I)

wherein $R^7$ and $R^8$ each represent the same or different, linear or branched alkyl group, alkoxy group or alkanoyloxy group each of 1 to 18 carbon atoms, or the formula

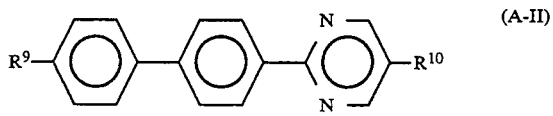 (A-II)

wherein $R^9$ and $R^{10}$ each represent the same or different, linear or branched alkyl group or alkoxy group each of 1 to 18 carbon atoms, the above-mentioned compounds having a smectic C phase.

(3) A ferroelectric smectic C liquid crystal composition according to item (1), wherein the component B is at least one Compound selected from among optically active compounds expressed by either one of the following three formulas, the above-mentioned optically active compounds having to one another, the same sense of the spontaneous polarizations in a chiral smectic C phase induced when dissolved in smectic C liquid crystal;

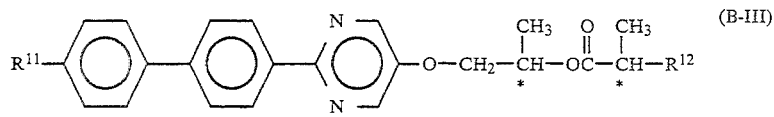  (B-III)

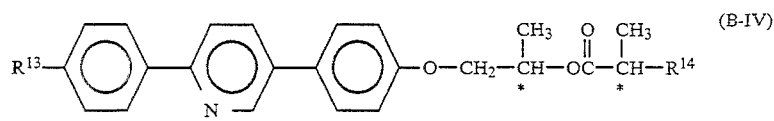  (B-IV)

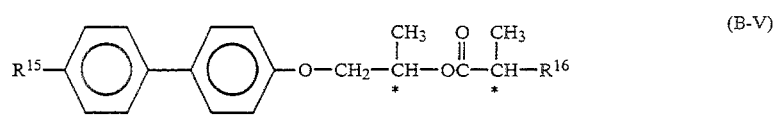  (B-V)

wherein $R^{11}$, $R^{13}$ and $R^{15}$ each independently represent a linear or branched alkyl group or alkoxy group each of 1 to 18 carbon atoms, $R^{12}$, $R^{14}$ and $R^{16}$ each independently represent a linear or branched alkyl group of 2 to 18 carbon atoms or a linear or branched alkoxy group of 1 to 18 carbon atoms and the symbol * represents an asymmetric carbon atom.

(4) A ferroelectric smectic C liquid crystal composition according to item (1), wherein the component C is at least one compound selected from among optically active compounds expressed by the formula

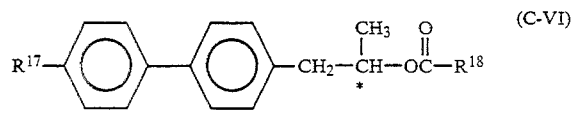  (C-VI)

wherein $R^{17}$ and $R^{18}$ each independently represent a linear or branched alkyl group or alkoxy group each of 1 to 18 carbon atoms and the symbol * represents an asymmetric carbon atom, the above-mentioned optically active compounds having the same sense of the spontaneous polarization in a chiral smectic C phase induced when dissolved in smectic C liquid crystal, as the sense of the compound of the component B.

(5) A ferroelectric smectic C liquid crystal composition according to item (1), wherein the component A is at least one compound selected from among compounds expressed by the formula

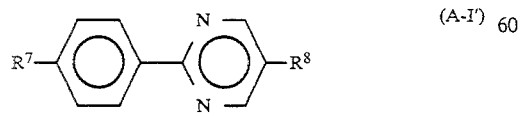  (A-I')

wherein $R^7$ represents a linear alkyl group, alkoxy group or alkanoyloxy group each of 5 to 14 carbon atoms and $R^8$ represents a linear alkyl group or alkoxy group each of 4 to 16 carbon atoms, or the formula

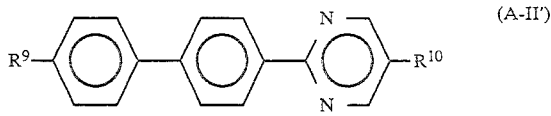  (A-II')

wherein $R^9$ and $R^{10}$ each independently represent a linear alkyl group or alkoxy group each of 5 to 10 carbon atoms, and having a smectic C phase.

(6) A ferroelectric smectic C liquid crystal composition according to item (1), wherein the component A is at least one compound selected from among compounds expressed by the formula

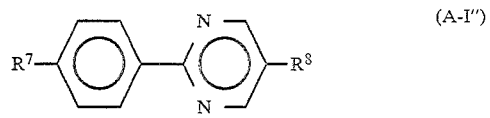  (A-I'')

wherein $R^7$ represents a linear alkyl group or alkoxy group each of 6 to 12 carbon atoms and $R^8$ represents a linear alkoxy group of 6 to 15 carbon atoms, or the formula

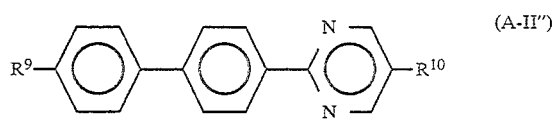  (A-II'')

wherein $R^9$ represents a linear alkyl group or alkoxy group each of 5 to 8 carbon atoms and $R^{10}$ represents a linear alkyl group of 6 to 8 carbon atoms, and having a smectic C phase.

(7) A ferroelectric smectic C liquid crystal composition according to item (1), wherein the component A is at least one compound selected from among compounds expressed by the formula

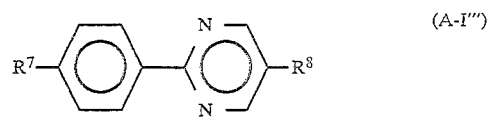  (A-I''')

wherein $R^7$ represents an alkyl group of 7 to 14 carbon atoms and $R^8$ represents an alkyl group of 10 to 14 carbon atoms, or the formula

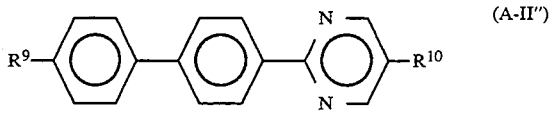 (A-II″)

wherein R⁹ represents a linear alkyl group or alkoxy group each of 5 to 8 carbon atoms and R¹⁰ represents a linear alkyl group of 6 to 8 carbon atoms, and having a smectic C phase.

(8) A ferroelectric smectic C liquid crystal composition according to item (1), wherein the component B is at least one compound selected from among optically active compounds expressed by either one of the following three formulas, the above-mentioned optically active compounds having to one another, the same sense of the spontaneous polarization in a chiral smectic C phase induced when dissolved in smectic C liquid crystal;

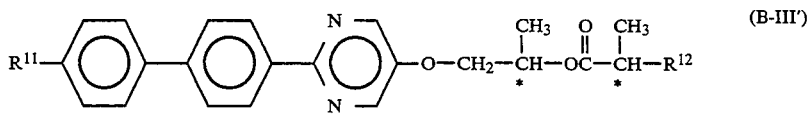 (B-III′)

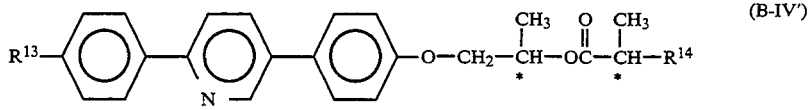 (B-IV′)

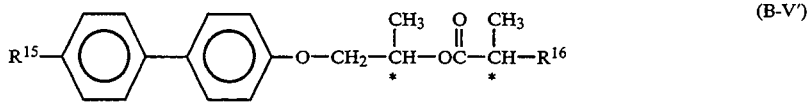 (B-V′)

wherein R¹¹ and R¹³ each independently represent a linear alkyl group or alkoxy group each of 3 to 10 carbon atoms, R¹⁵ represents a linear alkyl group or alkoxy group each of 3 to 12 carbon atoms, R¹², R¹⁴ and R¹⁶ each independently represent a linear alkyl group or alkoxy group each of 2 to 10 carbon atoms and the symbol * represents an asymmetric carbon atom.

(9) A ferroelectric smectic C liquid crystal composition according to item (1), wherein the component C is at least one compound selected from among compounds expressed by the formula

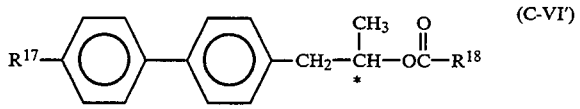 (C-VI′)

wherein R¹⁷ represents a linear alkoxy group of 3 to 10 carbon atoms, R¹⁸ represents an alkyl group of 2 to 6 carbon atoms and the symbol * represents an asymmetric carbon atom, the above-mentioned optically active compounds having the same sense of the spontaneous polarization in a chiral smectic C phase induced when dissolved in smectic C liquid crystal, as the sense of the compound of the component B.

(10) A ferroelectric smectic C liquid crystal composition according to item (1), wherein the component A is a smectic C liquid crystal mixture consisting of

| | |
|---|---|
| 2-(4-octylphenyl)-5-undecylpyrimidine | 35% by weight, |
| 2-(4-pentylbiphenyl-4′-yl)-5-hexylpyrimidine | 25% by weight, |
| 2-(4-hexylbiphenyl-4′-yl)-5-hexylpyrimidine | 6% by weight, |
| 2-(4-heptylbiphenyl-4′-yl)-5-hexylpyrimidine | 31% by weight, and |
| 2-(4-octylbiphenyl-4′-yl)-5-hexylpyrimidine | 3% by weight. |

(11) A ferroelectric smectic C liquid crystal composition according to item (1), wherein the component B is a compound expressed by the formula

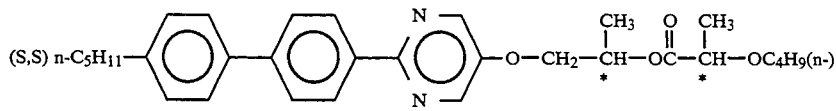

and the component C is a compound expressed by the formula

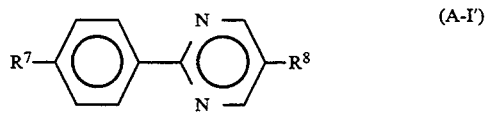 (R)

(12) A light-switching element containing a ferroelectric smectic C liquid crystal composition as set forth in any one of the above items (1) to (11).

DETAILED DESCRIPTION OF PREFERRED EMBODIMENTS

The compound expressed by the formula (A) as the component A of the liquid crystal composition of the present invention is a known compound abundant in smectic C liquid crystallinity. Such a compound is a substance which imparts a SC* phase to a ferroelectric liquid crystal over a broad temperature range (hereinafter referred to as a base SC compound). As the component A, compounds expressed by the formula (A-I′)

wherein R⁷ represents a linear alkyl group, alkoxy group or alkanoyloxy group each of 5 to 14 carbon atoms and $R^8$ represents a linear alkyl group or alkoxy group each of 4 to 16 carbon atoms, or the formula

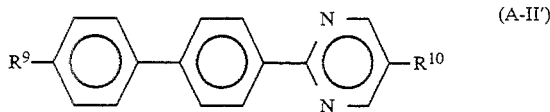

wherein $R^9$ and $R^{10}$ each independently represent a linear alkyl group or alkoxy group each of 5 to 10 carbon atoms are preferably used.

As the component A, a pyrimidine compound expressed by the formula (A-I') or a pyrimidine compound expressed by the formula (A-II') may be used singly, but simultaneous use of the compound of the formula (A-I') with the compound of the formula (A-II') is preferred, and use of a blend of a plurality of the former compounds with a plurality of the latter compounds is more preferred.

The compound of the formula (A-I') exhibits the SC phase within a relatively low temperature range, while the compound expressed by the formula (A-II') exhibits the SC phase within a relatively high temperature range. For example, a phenylpyrimidine compound (A-1) of the formula (A-I') wherein $R^7$ represents n-$C_6H_{13}O$— and $R^8$ represents n-$C_8H_{17}$-exhibits the following phase transition points (°C.):

wherein Cr, SA, N and Iso mean the respective phases of crystal, smectic A, nematic and isotropic liquid and the numeral figures therebetween show the phase transition points. Further, a biphenylylpyrimidine compound (A-35) expressed by the formula (A-II') wherein $R^9$ represents n-$C_7H_{15}$ and $R^{10}$ represents n-$C_8H_{17}$- exhibits the following phase transition points:

Thus, by using a plurality of phenylpyrimidine compounds together with a plurality of biphenylylpyrimidine compounds, it is possible to obtain a base SC mixture exhibiting SC phase within a broad temperature range including room temperature.

It is required for the ferroelectric liquid crystal composition of the present invention to exhibit the SA phase and N* phase, besides the SC* phase capable of exhibiting ferroelectricity; hence as the component A compound, compounds exhibiting these three liquid crystal phases are more preferably used.

In the case where compounds exhibit either the SA or N phase (but not both) or where both phases are absent, and where such compounds are used as the base SC compound, when compounds exhibiting the SA phase or N phase within a broad range are mixed with the above compounds, it is possible to cause the objective ferroelectric composition to exhibit these three liquid crystal phases. As the compounds exhibiting the SA phase or N phase, used in this case, it is preferred to mix compound of the component B or component A, abundant in smectic A liquid crystallinity or cholesteric properties, and in many cases, a biphenylylpyrimidine compound expressed by the formula (A-II) is preferably used.

Usually, in the simultaneous use of the compound of the formula (A-I) with that of the formula (A-II) to prepare component A, the proportion of the compound of the formula (A-I) based upon the total quantity of both the compounds is preferably 70% by weight or less, more preferably 30 to 60% by weight.

As a particularly preferable substance as the component A, there is illustrated a base SC mixture containing at least one compound of the formula (A-I') wherein $R^7$ represents a linear alkyl group of 6 to 12 carbon atoms and $R^8$ represents a linear alkoxy group of 4 to 15 carbon atoms or $R^7$ represents an alkyl group of 7 to 14 carbon atoms and $R^8$ represents an alkyl group of 10 to 14 carbon atoms and at least one compound of the formula (A-II') wherein $R^9$ represents a linear alkyl group or alkoxy group each of 5 to 8 carbon atoms and $R^{10}$ represents a linear alkyl group of 6 to 8 carbon atoms.

The component A plays a role as a base SC mixture and also a role by which the resulting ferroelectric liquid crystal composition exhibits the SA phase and N* phase besides the SC* phase; thus, the proportion of the component A in the ferroelectric composition of the present invention is preferably 55% by weight or more. If the proportion of the component A is less than 55% by weight based upon the total weight of the composition, the content of the optically active compound not always having all of the above three liquid crystal phases becomes relatively high, so that the N* phase or the SA phase is often undesirably extinct in the resulting ferroelectric composition.

Phenylpyrimidine compounds and biphenylylpyrimidine compounds, preferably used as the component A, are illustrated below in Tables 1 and 2.

TABLE 1

Compounds expressed by the formula

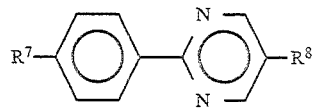

| $R^7$ | $R^8$ |
|---|---|
| $C_6H_{13}O$— | $C_8H_{17}$— |
| ″ | $C_9H_{19}$— |
| ″ | $C_{10}H_{21}$— |
| ″ | $C_{11}H_{23}$— |
| $C_8H_{17}O$— | $C_9H_{19}$— |
| ″ | $C_{10}H_{21}$— |
| ″ | $C_{11}H_{23}$— |
| $C_9H_{19}O$— | $C_7H_{15}$— |
| ″ | $C_8H_{17}$— |
| ″ | $C_9H_{19}$— |
| ″ | $C_{10}H_{21}$— |
| $C_{10}H_{21}O$— | $C_8H_{17}$— |
| $C_{11}H_{23}O$— | $C_7H_{15}$— |
| ″ | $C_8H_{17}$— |
| $C_7H_{15}O$— | $C_9H_{19}$— |
| ″ | $C_{10}H_{21}$— |
| ″ | $C_{11}H_{23}$— |
| $C_8H_{17}O$— | $C_8H_{17}$— |
| $C_{12}H_{25}O$— | $C_7H_{15}$— |
| ″ | $C_8H_{17}$— |
| $C_5H_{11}COO$— | $C_8H_{17}$— |
| $C_6H_{13}COO$— | ″ |
| $C_7H_{15}COO$— | ″ |
| $C_8H_{17}COO$— | ″ |
| $C_9H_{19}COO$— | ″ |
| $C_{10}H_{21}COO$— | ″ |
| $C_{11}H_{23}COO$— | ″ |
| $C_6H_{13}$— | $C_7H_{15}O$— |
| ″ | $C_8H_{17}O$— |
| ″ | $C_9H_{19}O$— |
| ″ | $C_{10}H_{21}O$— |

TABLE 1-continued

Compounds expressed by the formula

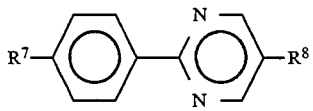

| $R^7$ | $R^8$ |
|---|---|
| " | $C_{11}H_{23}O-$ |
| " | $C_{12}H_{25}O-$ |
| " | $C_{13}H_{27}O-$ |
| " | $C_{14}H_{29}O-$ |
| " | $C_{15}H_{31}O-$ |
| $C_7H_{15}-$ | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_8H_{17}-$ | $C_7H_{15}O-$ |
| " | $C_8H_{17}O-$ |
| $C_8H_{17}-$ | $C_9H_{19}O-$ |
| " | $C_{10}H_{21}O-$ |
| " | $C_{11}H_{23}O-$ |
| " | $C_{12}H_{25}O-$ |
| " | $C_{13}H_{27}O-$ |
| $C_9H_{19}-$ | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| " | $C_{13}H_{27}O-$ |
| $C_{10}H_{21}-$ | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_5H_{11}O-$ | $C_6H_{13}O-$ |
| " | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_6H_{13}O-$ | $C_6H_{13}O-$ |
| " | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_9H_{19}O-$ | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_{10}H_{21}O-$ | $C_6H_{13}O-$ |
| " | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_{11}H_{23}O-$ | $C_6H_{13}O-$ |
| $C_7H_{15}O-$ | $C_6H_{13}O-$ |
| " | $C_7H_{15}O-$ |
| " | $C_8H_{17}O-$ |
| " | $C_9H_{19}O-$ |
| " | $C_{10}H_{21}O-$ |
| " | $C_{10}H_{23}O-$ |
| " | $C_{12}H_{25}O-$ |
| $C_8H_{17}O-$ | $C_6H_{13}O-$ |
| " | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| $C_9H_{19}O-$ | $C_6H_{13}O-$ |
| $C_{11}H_{23}O-$ | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| " | $C_{16}H_{33}O-$ |
| $C_{12}H_{25}O-$ | $C_6H_{13}O-$ |
| " | $C_7H_{15}O-$ |
| " | $C_8H_{17}O-$ |
| " | $C_9H_{19}O-$ |
| " | $C_{10}H_{21}O-$ |
| " | $C_{11}H_{23}O-$ |
| " | $C_{12}H_{25}O-$ |
| " | $C_{16}H_{33}O-$ |
| $C_7H_{15}-$ | $C_9H_{19}-$ |
| " | $C_{10}H_{21}-$ |
| " | $C_{11}H_{23}-$ |
| " | $C_{12}H_{25}-$ |
| " | $C_{14}H_{29}-$ |
| $C_8H_{17}-$ | $C_9H_{19}-$ |
| " | $C_{10}H_{21}-$ |
| " | $C_{11}H_{23}-$ |
| " | $C_{12}H_{25}-$ |
| " | $C_{14}H_{29}-$ |
| $C_9H_{19}-$ | $C_{10}H_{21}-$ |
| " | $C_{12}H_{25}-$ |
| $C_{10}H_{21}-$ | $C_{10}H_{21}-$ |
| " | $C_{11}H_{23}-$ |
| " | $C_{12}H_{25}-$ |
| $C_{12}H_{25}-$ | $C_{11}H_{23}-$ |
| " | $C_{12}H_{25}-$ |

TABLE 2

Compounds expressed by the formula

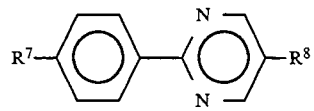

| $R^9$ | $R^{10}$ |
|---|---|
| $C_5H_{11}-$ | $C_6H_{13}-$ |
| " | $C_7H_{15}-$ |
| " | $C_8H_{17}-$ |
| $C_6H_{13}-$ | $C_6H_{13}-$ |
| " | $C_7H_{15}-$ |
| " | $C_8H_{17}-$ |
| $C_7H_{15}-$ | $C_6H_{13}-$ |
| " | $C_7H_{15}-$ |
| " | $C_8H_{17}-$ |
| $C_8H_{17}-$ | $C_6H_{13}-$ |
| " | $C_7H_{15}-$ |
| " | $C_8H_{17}-$ |
| $C_5H_{11}O-$ | $C_6H_{13}-$ |
| " | $C_7H_{15}-$ |
| " | $C_8H_{17}-$ |
| $C_6H_{13}O-$ | $C_6H_{13}-$ |
| " | $C_7H_{15}-$ |
| " | $C_8H_{17}-$ |
| $C_7H_{15}O-$ | $C_6H_{13}-$ |
| " | $C_7H_{15}-$ |
| " | $C_8H_{17}-$ |
| $C_8H_{17}O-$ | $C_6H_{13}-$ |
| " | $C_7H_{15}-$ |
| " | $C_8H_{17}-$ |

As the component A of the present invention, liquid crystal mixtures exhibiting the smectic C phase are preferably used. Examples of such mixtures are the following (a) and (b):

(a) a smectic C liquid crystal mixture comprising at least two components having the smectic C phase, at least one of which is expressed by the formula

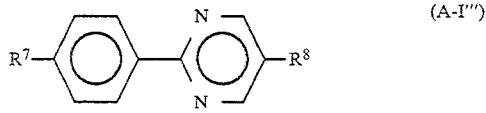

wherein $R^7$ represents an alkyl group of 7 to 14 carbon atoms and $R^8$ represents an alkyl group of 10 to 14 carbon atoms, and having the smectic C phase, and (b) a smectic C liquid crystal mixture comprising at least two components having the smectic C phase, one of which is a compound described above in (a) and one of which is a compound expressed by the formula

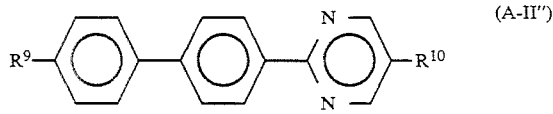

wherein $R^9$ represents a linear alkyl group of 5 to 8 carbon atoms and $R^{10}$ represents a linear alkyl group of 6 to 8 carbon atoms, and having a smectic C phase.

The 2-(4-alkylphenyl)-5-alkylpyrimidine compound described above in (a) is a novel compound having a smectic C phase, invented by Saito et al (Japanese patent application No. Hei 2-112598). This compound is particularly superior in the electrooptical response of the resulting ferroelectric liquid crystal composition as compared with known phenylpyrimidine compounds having two six-membered rings.

As a component of the base smectic C liquid crystal mixture in the present invention, a biphenylylpyrimidine compound expressed by the formula (A-II″) is preferably used besides a phenylpyrimidine compound expressed by the formula (A-I‴). If the base smectic C mixture is composed only of phenylpyrimidine compounds, the resulting mixture often has a SC phase within a relatively low temperature range and also often is deficient in the N phase. In order to broaden the SC phase temperature region toward the higher temperature side or induce the N phase to thereby overcome the above defects, a biphenylylpyrimidine compound is preferably used.

The component B contributes to the high speed properties of the electrooptical response of the ferroelectric liquid crystal composition of the present invention. As the compound of the component B, optically active compounds expressed by the above-described formulas (B-III), (B-IV) or (B-V) are preferably used. These compounds are known for example in Japanese patent application laid-open Nos. Sho 63-267763, Sho 64-63571 and Sho 64-50, and most of the compounds have SC* phase and also have a large spontaneous polarization. For example, a compound B-1 of the formula (B-III) wherein $R^{11}$ and $R^{12}$ both represent -OC$_6$H$_{13}$(n-) and a compound B-9 of the formula (B-IV) wherein $R^{13}$ represents n-C$_9$H$_{19}$- and $R^{14}$ represents -OC$_3$H$_7$(n-) have the following phase transition points, respectively:

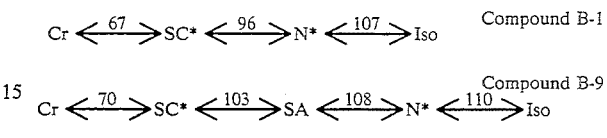

and the spontaneous polarization value, tilt angle and response time (impressed voltage: 5 V/μm), at a temperature (T) lower by 10° C. than the upper limit temperature of SC* phase (Tc) are shown in the following Table 3:

TABLE 3

|  | B-1 | B-9 |
|---|---|---|
| Spontaneous polarization (nC/cm²) | 327 | 243 |
| Tilt angle (°) | 45 | 38 |
| Response time (μsec) | 45 | 30 |

Further, even when the optically active compounds expressed by these formulas, have no liquid crystal phase by themselves, they induce a large spontaneous polarization in a SC* phase formed when they are dissolved in a SC liquid crystal phase; hence they serve the high speed response of the composition of the present invention.

Examples of optically active compounds particularly preferred as the component B are as follows:

a compound of the formula (B-III) wherein $R^{11}$ represents a linear alkyl group or alkoxy group each of 3 to 10 carbon atoms and $R^{12}$ represents a linear alkyl group or alkoxy group each of 2 to 10 carbon atoms, a compound of the formula (B-IV) wherein $R^{13}$ represents a linear alkyl group or alkoxy group each of 3 to 10 carbon atoms and $R^{14}$ represents a linear alkyl group or alkoxy group each of 2 to 10 carbon atoms, and a compound of the formula (B-V) wherein $R^{15}$ represents a linear alkyl group or alkoxy group each of 3 to 10 carbon atoms and $R^{16}$ represents a linear alkyl group or alkoxy group each of 2 to 10 carbon atoms. These compounds are illustrated in the following Tables 4, 5 and 6:

TABLE 4

Compounds expressed by the formula

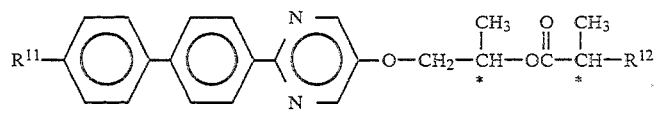

| $R^{11}$ | $R^{12}$ | $R^{11}$ | $R^{12}$ |
|---|---|---|---|
| C$_5$H$_{11}$— | —C$_2$H$_5$ | C$_6$H$_{13}$— | —OC$_5$H$_{11}$ |
| C$_5$H$_{11}$— | —C$_6$H$_{13}$ | C$_3$H$_7$— | —OC$_6$H$_{13}$ |
| C$_3$H$_7$— | —OC$_4$H$_9$ | C$_6$H$_{13}$— | —OC$_6$H$_{13}$ |
| C$_5$H$_{11}$— | —OC$_4$H$_9$ | C$_6$H$_{13}$O— | —OC$_4$H$_9$ |
| C$_6$H$_{13}$— | —OC$_4$H$_9$ | C$_6$H$_{13}$O— | —OC$_6$H$_{13}$ |

TABLE 4-continued

Compounds expressed by the formula $R^{11}\text{-}\bigcirc\text{-}\bigcirc\text{-}\bigcirc(N,N)\text{-}O\text{-}CH_2\text{-}\overset{CH_3}{\underset{*}{CH}}\text{-}O\overset{O}{C}\text{-}\overset{CH_3}{\underset{*}{CH}}\text{-}R^{12}$

| $R^{11}$ | $R^{12}$ | $R^{11}$ | $R^{12}$ |
|---|---|---|---|
| $C_7H_{15}-$ | $-OC_4H_9$ | | |

TABLE 5

Compounds expressed by the formula $R^{13}\text{-}\bigcirc\text{-}\bigcirc(N)\text{-}\bigcirc\text{-}O\text{-}CH_2\text{-}\overset{CH_3}{\underset{*}{CH}}\text{-}O\overset{O}{C}\text{-}\overset{CH_3}{\underset{*}{CH}}\text{-}R^{14}$

| $R^{13}$ | $R^{14}$ | $R^{13}$ | $R^{14}$ |
|---|---|---|---|
| $C_6H_{13}-$ | $-C_2H_5$ | $C_6H_{13}-$ | $-OC_3H_7$ |
| $C_7H_{15}-$ | $-C_2H_5$ | $C_7H_{15}-$ | $-OC_3H_7$ |
| $C_9H_{19}-$ | $-C_2H_5$ | $C_9H_{19}-$ | $-OC_3H_7$ |
| $C_5H_{11}-$ | $-OC_3H_7$ | $C_7H_{15}-$ | $-OC_4H_9$ |

TABLE 6

Compounds expressed by the formula $R^{15}\text{-}\bigcirc\text{-}\bigcirc\text{-}O\text{-}CH_2\text{-}\overset{CH_3}{\underset{*}{CH}}\text{-}O\overset{O}{C}\text{-}\overset{CH_3}{\underset{*}{CH}}\text{-}R^{12}$

| $R^{15}$ | $R^{16}$ |
|---|---|
| $C_7H_{15}-$ | $-OC_3H_7$ |
| $C_8H_{17}-$ | $-OC_3H_7$ |
| $C_6H_{13}O-$ | $-OC_3H_7$ |
| $C_8H_{17}O-$ | $-OC_3H_7$ |
| $C_8H_{17}O-$ | $-OC_4H_9$ |
| $C_{10}H_{21}O-$ | $-OC_6H_{13}$ |
| $C_{11}H_{23}O-$ | $-OC_4H_9$ |

As to the compound expressed by the formula (B), when the absolute configuration at its optically active site is of (S,S) type or (S,R) type, the polarity of the spontaneous polarization is of −type and the helical twist sense is left-handed (while when the absolute configuration is of (R,R) type or (R,S) type, the polarity is of +type and the helical twist sense is right-handed).

In the present invention, when a plurality of optically active compounds are used as the component B, the component B is composed of optically active compounds wherein the polarities of the spontaneous polarization induced by the compounds are the same. When the polarities of a plurality of the compound of component B are made same, the high speed electrooptical response of the ferroelectric liquid crystal composition of the present invention is preferably realized, When two or more optically active compounds having different polarities of spontaneous polarization are used as the component B, the spontaneous polarization values are offset so that it is often impossible to achieve the high speed response of the resulting ferroelectric composition, which is undesirable.

The component B plays an important role of causing the high speed response properties to appear, in the ferroelectric liquid crystal composition sought in the present invention, but its use in too a large quantity has a bad influence upon the phase series of the liquid crystal composition and the spontaneous polarization values becomes so large that there is a possibility that an abnormal phenomenon occurs at the time of switching (e.g. see Akio Yoshida et al: the 13th Japan Liquid Crystal Symposium, p. 142-143 (1987)); hence the concentration of the component B is preferably 25% by weight or less.

When the component B is composed of optically active compounds having opposite polarities of the spontaneous polarization to each other, the spontaneous polarization in the resulting ferroelectric composition lowers or the content of the component B is required to increase; hence this has an undesirable influence upon the resulting composition.

Besides the compounds expressed by the respective formulas (B-III), (B-IV) and (B-V), optically active compounds expressed by the following formulas may be used as compounds of the component B:

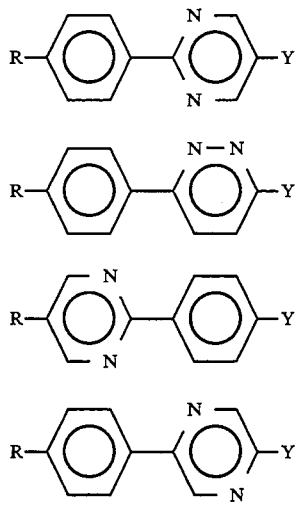

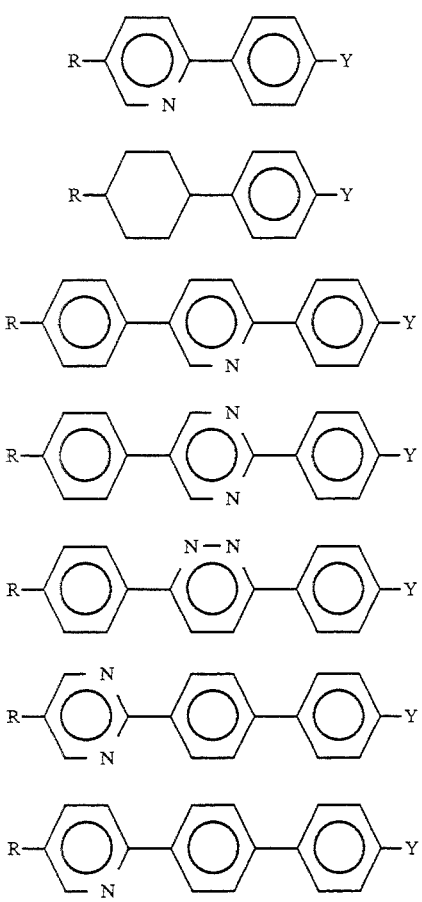

In these formulas, R represents an alkyl group or alkoxy group each of 3 to 14 carbon atoms, Y represents

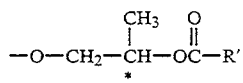

and R' represents an alkyl group of 2 to 6 carbon atoms. The optically active compounds expressed by these formulas are known in the above-mentioned Japanese laid-open patent applications.

The component C described above in the item (1) is represented by the formula (C), and is composed of optically active compounds having the same polarity of the spontaneous polarization induced by the compounds in the SC* phase, as that of the compound(s) of the component B. At that time, the optically active compound(s) of the component C functions as a helical pitch-adjusting agent upon the optically active compound(s) of the component B, and plays a role of elongating the helical pitches in the SC* phase and N* phase of the liquid crystal composition of the present invention.

As compounds preferably used as the component C, optically active compounds of the formula (C-VI) wherein $R^{17}$ and $R^{18}$ each represent a linear alkyl group or alkoxy group may be mentioned. As a particularly preferable compound, an optically active compound of the above formula wherein $R^{17}$ represents a linear alkoxy group of 3 to 10 carbon atoms and $R^{18}$ represents a linear alkyl group of 2 to 6 carbon atoms may be mentioned. These compounds of the formula (C-VI) are disclosed in Japanese patent application laid-open No. Sho 64-49. Examples of the compounds of the component C are shown in Table 7.

TABLE 7

Compounds expressed by the formula

| $R^{17}$ | $R^{18}$ |
|---|---|
| $C_7H_{15}O-$ | $C_3H_7-$ |
| $C_8H_{17}O-$ | $C_5H_{11}-$ |
| $C_8H_{17}-$ | $C_4H_9-$ |
| $C_{10}H_{21}-$ | $C_2H_5-$ |
| $C_8H_{17}O-$ | $C_4H_9-$ |
| $C_9H_{19}O-$ | $C_4H_9-$ |
| $C_8H_{17}O-$ | $C_6H_{13}-$ |
| $C_8H_{17}O-$ | $C_2H_5-$ |
| $C_8H_{17}O-$ | $C_3H_7-$ |
| $C_8H_{17}O-$ | $C_7H_{15}-$ |

As to the compound expressed by the formula (C), when the absolute configuration at the optically active site is of the R type, the polarity of the spontaneous polarization is of −type and the helical twist sense is right-handed (while when the absolute configuration is of the S type, the polarity is of +type and the helical twist sense is left-handed). Thus, when a compound of the component B expressed by the formula (B) has an absolute configuration of (S,S) or (S,R) type, then combination of the compound with a compound of the component C, expressed by the formula (C), having an absolute configuration of R type affords a ferroelectric liquid crystal composition having a long helical pitch.

Further, when a compound of the component B expressed by the formula (B) has an absolute configuration of (R,R) or (R,S) type, mixing of the compound with a compound of the component C, expressed by the formula (C), having an absolute configuration of S type may adjust the helical pitch of the mixture.

The component C functions mainly as a helical pitch-adjusting agent upon the component B in the ferroelectric liquid crystal composition aimed in the present invention, and plays a role of elongating the helical pitch without damaging the response properties of the liquid crystal composition, but its use in too large a quantity lowers the upper limit temperature of SC* phase or since the component C is poor in the liquid crystallinity, the above use has a bad influence upon the Iso-N*-SA-SC* type series; hence the concentration of the component C is preferably 20% by weight or less.

The ferroelectric liquid crystal composition of the present invention is based upon a skillful combination of the above superior characteristics of the component A, component B and component C. In particular, the ferroelectric composition of the present invention is characterized by combining the compound of component C with the compound of component B with the main aim of adjusting the helical pitches in SC* and N* phases to achieve a quick electrooptical response in a light-switching device.

Ferroelectric liquid crystal compositions containing a compound of the formula (A-I) or the formula (A-II) suitable as the base SC compound and an optically active liquid crystal of the formula (B-III), the formula (B-IV) or the formula (B-V) have already been disclosed by the present inventors in Japanese patent applications laid-open Nos. Hei 2-145683 or Hei 2-265986. The difference between these ferroelectric compositions and the present invention consists in that in the present invention, another optically active compound having an opposite helical twist sense to those of the optically active compounds (B-III)-(B-V) is used for adjusting the helical pitch of the resulting composition.

Examples of these two different ferroelectric liquid crystal compositions are described in Example 1 and Comparative example 1 mentioned below, respectively. In these Examples, it is shown that superior response properties are obtained by adding an optically active compound of the formula (C-VI) with an aim of adjusting the helical pitch of the resulting composition.

The contents of the respective components A, B and C in the ferroelectric liquid crystal composition of the present invention, skillfully making use of the characteristics of the respective components, are as follows: that of component A: 55–91% by weight, that of component B: 5–25% by weight, and that of component C: 4–20% by weight. If the contents of the component B and component C are lower than 5% by weight and 4% by weight, respectively, it is impossible to achieve the high speed response of the resulting composition. The component B and the component C have opposite helical twist senses to each other to function so as to offset the helical twistabilities in the SC* phase and N* phase; hence the proportions of the contents thereof are particularly preferred to be 0.5 to 2 parts by weight of component C per one part by weight of component B.

EXAMPLE

The present invention will be described in more detail by way of Examples, but it should not be construed to be limited thereto.

Various measurements in the following examples were carried out according to the following methods:

Spontaneous polarization value (Ps) was measured according to the Sawyer-Tower method. Tilt angle ($\theta$) was sought by microscopic observation of a homogeneously aligned liquid crystal cell on a rotating stage under crossed nicol prisms in which observation of an extinction position is determined by first impressing an electric field sufficiently higher than the critical voltage to unwind the helical structure of the liquid crystal, followed by reversing the polarity of the impressed field to obtain another extinction position, to afford an angle (corresponding to 2 $\theta$) by rotating the stage from the first extinction position to the other extinction position.

Response time was sought by placing the respective compositions in a cell subjected to an aligning treatment and having a gap between electrodes of 2 μm, followed by measuring the change in the intensity of transmitted light at the time of impressing a square wave of 1 KHz under a peak to peak voltage Vpp of 20 V in Examples 1–9 and 26–29, and Comparative examples 1–3, but in Examples 12–14 and 17–25, the response time was sought in a similar manner to the above except that the above voltage of 20 V was replaced by 40 V.

SC* pitch was sought by directly measuring the distance between dechiralization lines corresponding to the helical pitch under a polarizing microscope, using a cell of about 200 μm in cell thickness subjected to homogeneous alignment.

The measurements of the above Ps, $\theta$, response time and SC* pitch were all carried out at 25° C. and the measurement of N* pitch described below was carried out at a temperature higher by 1° C. than the lower limit of N* phase.

N* pitch was indirectly sought by measuring the distance (l) between disclination lines under a polarizing microscope using a wedge type cell, and employing a theoretical equation of $P(pitch) = 2l \cdot \tan\theta$ where $\theta$ represents the angle of the wedge.

In the Examples and Comparative examples mentioned below, the designation of the compounds used as component compounds of the liquid crystal compositions was made by compound numbers, and these compound numbers are described in Tables 8–13, besides compounds previously described.

TABLE 8

| Compound No. | In Formula (A-I) R$^7$ | R$^8$ |
|---|---|---|
| A-1 | n-C$_6$H$_{13}$O— | n-C$_8$H$_{17}$— |
| A-2 | n-C$_8$H$_{17}$O— | n-C$_8$H$_{17}$— |
| A-3 | n-C$_9$H$_{19}$O— | n-C$_7$H$_{15}$— |
| A-4 | n-C$_9$H$_{19}$O— | n-C$_8$H$_{17}$— |
| A-5 | n-C$_{10}$H$_{21}$O— | n-C$_8$H$_{17}$— |
| A-6 | n-C$_6$H$_{13}$— | n-C$_8$H$_{17}$O— |
| A-7 | n-C$_6$H$_{13}$— | n-C$_9$H$_{19}$O— |
| A-8 | n-C$_7$H$_{15}$— | n-C$_8$H$_{17}$O— |
| A-9 | n-C$_7$H$_{15}$— | n-C$_9$H$_{19}$O— |
| A-10 | n-C$_8$H$_{17}$— | n-C$_9$H$_{19}$O— |
| A-11 | n-C$_8$H$_{17}$— | n-C$_{10}$H$_{21}$O— |
| A-12 | n-C$_{10}$H$_{21}$— | n-C$_{10}$H$_{21}$— |
| A-13 | n-C$_7$H$_{15}$— | n-C$_{11}$H$_{23}$— |
| A-14 | n-C$_9$H$_{19}$— | (CH$_3$)$_2$CH(CH$_2$)$_6$— |
| A-15 | (CH$_3$)$_2$CH(CH$_2$)$_6$— | n-C$_{10}$H$_{21}$— |
| A-16 | n-C$_{10}$H$_{21}$— | n-C$_{12}$H$_{25}$— |
| A-17 | n-C$_9$H$_{19}$— | n-C$_{10}$H$_{21}$— |
| A-18 | n-C$_7$H$_{15}$— | n-C$_8$H$_{17}$— |
| A-19 | n-C$_8$H$_{17}$— | n-C$_9$H$_{19}$— |
| A-20 | n-C$_8$H$_{17}$O— | n-C$_{10}$H$_{21}$— |
| A-21 | n-C$_8$H$_{17}$O— | n-C$_9$H$_{19}$— |
| A-22 | n-C$_{12}$H$_{25}$O— | n-C$_8$H$_{17}$— |
| A-23 | n-C$_8$H$_{17}$— | n-C$_{10}$H$_{21}$— |
| A-24 | n-C$_8$H$_{17}$— | n-C$_{11}$H$_{23}$— |

TABLE 9

| Compound No. | In Formula (A-II) R$^9$ | R$^{10}$ |
|---|---|---|
| A-31 | n-C$_5$H$_{11}$— | n-C$_6$H$_{13}$— |
| A-32 | n-C$_5$H$_{11}$— | n-C$_8$H$_{17}$— |
| A-33 | n-C$_6$H$_{13}$— | n-C$_6$H$_{13}$— |
| A-34 | n-C$_7$H$_{15}$— | n-C$_6$H$_{13}$— |
| A-35 | n-C$_7$H$_{15}$— | n-C$_8$H$_{17}$— |
| A-36 | n-C$_8$H$_{17}$— | n-C$_6$H$_{13}$— |

TABLE 10

| Compound No. | Absolute configuration at asymmetric center | In Formula (B-III) R$^{11}$ | R$^{12}$ |
|---|---|---|---|
| B-1 | (S, S) | n-C$_6$H$_{13}$O— | n-C$_6$H$_{13}$O— |
| B-2 | (S, S) | n-C$_3$H$_7$— | n-C$_4$H$_9$O— |
| B-3 | (S, S) | n-C$_5$H$_{11}$— | n-C$_4$H$_9$O— |
| B-4 | (S, S) | n-C$_5$H$_{11}$— | n-C$_6$H$_{13}$— |
| B-5 | (S, S) | n-C$_7$H$_{15}$— | n-C$_4$H$_9$O— |

TABLE 11

| Compound No. | Absolute configuration at asymmetric center | In Formula (B-IV) R¹³ | R¹⁴ |
|---|---|---|---|
| B-6 | (S, S) | n-C$_6$H$_{13}$— | n-C$_3$H$_7$O— |
| B-7 | (S, S) | n-C$_6$H$_{13}$— | C$_2$H$_5$ |
| B-8 | (S, S) | n-C$_7$H$_{15}$— | n-C$_4$H$_9$O— |
| B-9 | (S, S) | n-C$_9$H$_{19}$— | n-C$_3$H$_7$O— |

TABLE 12

| Compound No. | Absolute configuration at asymmetric center | In Formula (B-V) R¹⁵ | R¹⁶ |
|---|---|---|---|
| B-10 | (S, S) | n-C$_8$H$_{17}$O— | n-C$_4$H$_9$O— |
| B-11 | (S, S) | n-C$_{11}$H$_{23}$O— | n-C$_4$H$_9$O— |

TABLE 13

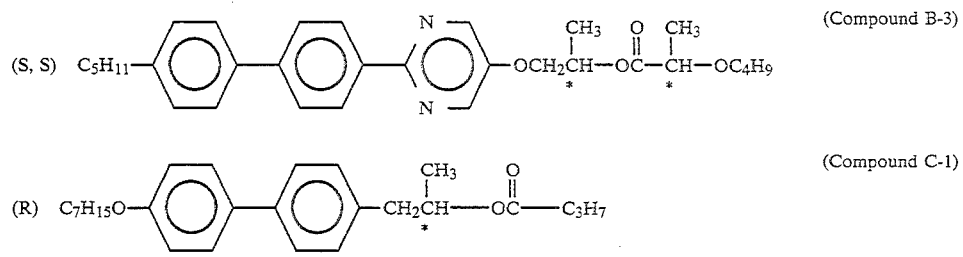

| Compound No. | Absolute configuration at asymmetric center | In Formula (C-VI) R¹⁷ | R¹⁸ |
|---|---|---|---|
| C-1 | (R) | n-C$_7$H$_{15}$O— | n-C$_3$H$_7$— |
| C-2 | (R) | n-C$_8$H$_{17}$O— | n-C$_5$H$_{11}$— |
| C-3 | (R) | n-C$_8$H$_{17}$— | n-C$_4$H$_9$— |
| C-4 | (R) | n-C$_{10}$H$_{21}$— | C$_2$H$_5$— |
| C-5 | (R) | n-C$_8$H$_{17}$O— | n-C$_4$H$_9$— |
| C-6 | (R) | n-C$_9$H$_{19}$O— | n-C$_4$H$_9$— |
| C-7 | (R) | n-C$_8$H$_{17}$O— | n-C$_6$H$_{13}$— |

Example 1

A base SC mixture I consisting of the following compounds was prepared:

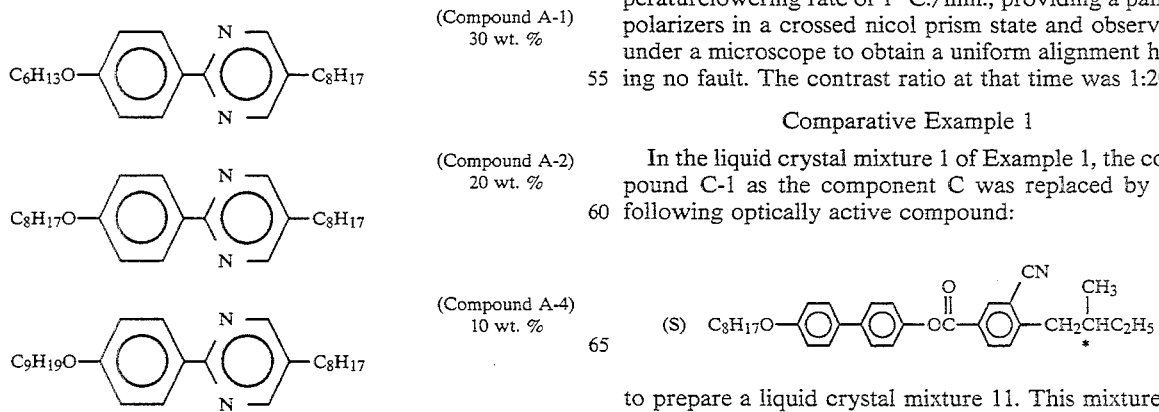

(Compound A-1) 30 wt. %

(Compound A-2) 20 wt. %

(Compound A-4) 10 wt. %

(Compound A-5) 10 wt. %

(Compound A-32) 20 wt. %

(Compound A-35) 10 wt. %

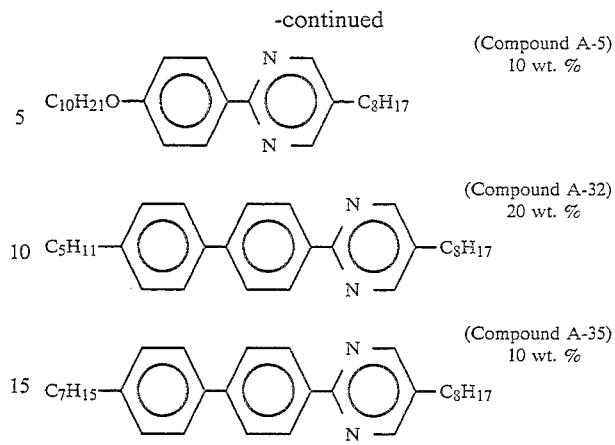

To this base mixture (80 parts by weight) were added the following compound B-3 as the component B and compound C-1 as the component C, each in 10 parts by weight, to prepare a liquid crystal mixture 1:

(Compound B-3)

(Compound C-1)

The phase transition points of this liquid crystal mixture 1 were as follows:

$$Cr \xrightarrow{-1° C.} SC^* \xrightarrow{53° C.} SA \xrightarrow{61° C.} N^* \xrightarrow{78° C.} Iso$$

Further, this mixture 1 exhibited a Ps of 25 nC/cm², a tilt angle of 23° and a response time of 80 μsec.

Further, the helical pitch in N* phase of the mixture 1 was 11 μm at 62° C., and that in SC* phase was 6 μm at 25° C.

In addition, this liquid crystal mixture was filled in a cell of 2 μm cell gap, provided with transparent electrodes having a polyimide as an aligning agent coated thereon, and then rubbing the surface to subject it to parallel aligning treatment, followed by gradually cooling the cell from N* phase toward SC* phase at a temperaturelowering rate of 1° C./min., providing a pair of polarizers in a crossed nicol prism state and observing under a microscope to obtain a uniform alignment having no fault. The contrast ratio at that time was 1:20.

Comparative Example 1

In the liquid crystal mixture 1 of Example 1, the compound C-1 as the component C was replaced by the following optically active compound:

to prepare a liquid crystal mixture 11. This mixture 11 exhibited the following phase transition points:

Further, this mixture exhibited a Ps value of 25 nC/cm$^2$, a tilt angle of 24° and a response time of 153 μsec, at 25° C. Further, the helical pitches in the SC* phase and the N* phase of the mixture were 5 μm at 25° C. and 9 μm at 78° C., respectively.

Example 2

A liquid crystal mixture 2 consisting of the following compounds was prepared:

| Compound A-6 | 7.8 wt. % |
|---|---|
| Compound A-8 | 7.8 wt. % |
| Compound A-10 | 7.8 wt. % |
| Compound A-11 | 7.8 wt. % |
| Compound A-31 | 11.7 wt. % |
| Compound A-33 | 11.7 wt. % |
| Compound A-34 | 11.7 wt. % |
| Compound A-36 | 11.7 wt. % |
| Compound B-3 | 12 wt. % |
| Compound C-1 | 10 wt. % |

This mixture exhibited the following phase transition points:

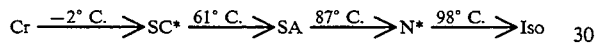

Further, this mixture exhibited a Ps value of 34 nC/cm$^2$, a tilt angle of 22° and a response time of 50 μsec. Further, the helical pitches in the N* phase was 50 μm or more, and that in the SC* phase was so long that the helical structure was not formed in a liquid crystal cell of 10 μm thick; thus the alignment was superior.

Example 3

A liquid crystal mixture 3 consisting of the following compounds of component A, 2 compounds of component B and one compound of component C was prepared:

| Compound A-6 | 10 wt. % |
|---|---|
| Compound A-7 | 5 wt. % |
| Compound A-8 | 5 wt. % |
| Compound A-9 | 5 wt. % |
| Compound A-10 | 5 wt. % |
| Compound A-11 | 5 wt. % |
| Compound A-31 | 5 wt. % |
| Compound A-32 | 10 wt. % |
| Compound A-33 | 10 wt. % |
| Compound A-34 | 10 wt. % |
| Compound A-36 | 10 wt. % |
| Compound B-3 | 5 wt. % |
| Compound B-4 | 5 wt. % |
| Compound C-2 | 10 wt. % |

The phase transition points, spontaneous polarization value, tilt angle, helical pitches in the SC* phase and N* phase and response time of the liquid crystal mixture 3 are shown in Table 14.

Example 4

A liquid crystal mixture 4 consisting of the following 8 compounds of component A, 2 compounds of component B and one compound of component C was prepared:

| Compound A-6 | 5 wt. % |
|---|---|
| Compound A-8 | 15 wt. % |
| Compound A-9 | 10 wt. % |
| Compound A-11 | 7 wt. % |
| Compound A-31 | 15 wt. % |
| Compound A-33 | 15 wt. % |
| Compound A-35 | 10 wt. % |
| Compound A-36 | 5 wt. % |
| Compound B-6 | 3 wt. % |
| Compound B-8 | 7 wt. % |
| Compound C-2 | 8 wt. % |

The phase transition points, spontaneous polarization value, tilt angle, helical pitches in the SC* phase and N* phase and response time of the liquid crystal mixture 4 are shown in Table 14.

Example 5

A liquid crystal mixture 5 consisting of the following 7 compounds of component A, 3 compounds of component B and 2 compounds of component C was prepared:

| Compound A-1 | 21 wt. % |
|---|---|
| Compound A-3 | 6 wt. % |
| Compound A-4 | 14 wt. % |
| Compound A-31 | 17 wt. % |
| Compound A-32 | 5 wt. % |
| Compound A-34 | 14 wt. % |
| Compound A-35 | 5 wt. % |
| Compound B-5 | 4 wt. % |
| Compound B-7 | 4 wt. % |
| Compound B-9 | 4 wt. % |
| Compound C-1 | 3 wt. % |
| Compound C-2 | 3 wt. % |

The characteristic values of the liquid crystal mixture 5 are shown in Table 14.

Example 6

A liquid crystal mixture 6 consisting of the following 8 compounds of component A, 3 compounds of component B and 2 compounds of component C was prepared:

| Compound A-7 | 7.3 wt.% |
|---|---|
| Compound A-8 | 7.3 wt. % |
| Compound A-10 | 7.3 wt. % |
| Compound A-11 | 7.3 wt. % |
| Compound A-31 | 11 wt. % |
| Compound A-33 | 11 wt. % |
| Compound A-34 | 11 wt. % |
| Compound A-36 | 10.8 wt. % |
| Compound B-2 | 7 wt. % |
| Compound B-9 | 5 wt. % |
| Compound B-10 | 3 wt. % |
| Compound C-1 | 5 wt. % |
| Compound C-2 | 7 wt. % |

The characteristic values of the liquid crystal mixture are shown in Table 14.

Example 7

A liquid crystal mixture 7 consisting of the following compounds of component A, 3 compounds of component B and one compound of component C was prepared:

| Compound A-1 | 12 wt. % |
|---|---|
| Compound A-2 | 8 wt. % |

-continued

| | |
|---|---|
| Compound A-4 | 4 wt. % |
| Compound A-5 | 4 wt. % |
| Compound A-7 | 4 wt. % |
| Compound A-9 | 4 wt. % |
| Compound A-10 | 4 wt. % |
| Compound A-11 | 4 wt. % |
| Compound A-31 | 6 wt. % |
| Compound A-32 | 8 wt. % |
| Compound A-33 | 6 wt. % |
| Compound A-34 | 6 wt. % |
| Compound A-35 | 4 wt. % |
| Compound A-36 | 6 wt. % |
| Compound B-2 | 3 wt. % |
| Compound B-9 | 8 wt. % |
| Compound B-11 | 2 wt. % |
| Compound C-1 | 7 wt. % |

The characteristic values of the liquid crystal mixture are shown in Table 14.

Example 8

A base SC mixture II consisting of compound A-7, compound A-8, compound A-10 and compound A-11, each in 10% by weight, and compound A-31, compound A-33, compound A-34 and compound A-35, each in 15% by weight, was prepared, followed by adding to this base SC mixture II (91 parts by weight), compound B-3 (5 parts by weight) and compound C-2 (4 parts by weight) to prepare a chiral smectic liquid crystal mixture 8.

The characteristic values of this liquid crystal mixture 8 are shown in Table 14.

Comparative Example 2

To the base SC mixture II (93 parts by weight) prepared in Example 8 were added compound B-3 (4 parts by weight) and compound C-2 (3 parts by weight) to prepare a chiral smectic liquid mixture 12. The characteristic values of this liquid crystal mixture 12 are shown in Table 14.

Example 9

Compound A-8, compound A-9, compound A-10 and compound A-11, each in 10% by weight, and compound. A-31, compound A-33, compound A-34 and compound A-36, each in 15% by weight, were mixed to prepare a base SC mixture III, followed by adding to this base SC mixture III (55 parts by weight), compound B-3 (8 parts by weight), compound B-8 (17 parts by weight) and compound C-2 (20 parts by weight), to prepare a chiral smectic liquid crystal mixture 9.

The characteristic values of this liquid crystal mixture 9 are shown in Table 14.

Comparative Example 3

To the base SC mixture III (48 parts by weight) used in Example 9 were added compound B-3 (10 parts by weight), compound B-8 (20 parts by weight) and compound C-2 (22 parts by weight), to prepare a liquid crystal mixture 13. The characteristic values of this liquid crystal mixture 13 are shown in Table 14.

TABLE 14

| Example | Phase transition point (°C.) Cr → SC* | SC* → SA | SA → N* | N* → Iso | Spontaneous polarization nC/cm$^2$ | Tilt angle (°) | Helical pitch (μm) SC* phase | N* phase | Response time (μsec) |
|---|---|---|---|---|---|---|---|---|---|
| Example 1 | <0 | 53 | 61 | 78 | 25 | 23 | 6 | 11 | 80 |
| Example 2 | −2 | 61 | 87 | 98 | 34 | 22 | >10 | 50 | 50 |
| Example 3 | −2 | 60 | 90 | 99 | 30 | 21 | 8 | 32 | 53 |
| Example 4 | −3 | 70 | 97 | 103 | 35 | 22 | 11 | 45 | 90 |
| Example 5 | −7 | 58 | 74 | 79 | 35 | 24 | 7 | 18 | 63 |
| Example 6 | −1 | 56 | 85 | 92 | 39 | 21 | 6 | 15 | 48 |
| Example 7 | −2 | 59 | 83 | 89 | 28 | 21 | 6 | 12 | 61 |
| Example 8 | −1 | 67 | 101 | 108 | 14 | 24 | 7 | 30 | 98 |
| Example 9 | 0 | 56 | 86 | 88 | 76 | 25 | 5 | 11 | 88 |
| Comp. ex. 1 | −5 | 66 | 77 | 89 | 25 | 24 | 5 | 9 | 153 |
| Comp. ex. 2 | −1 | 67 | 102 | 110 | 11 | 25 | 5 | 11 | 117 |
| Comp. ex. 3 | 2 | 53 | 87 | — | 83 | 26 | 2 | 7 | 123 |

Example 10

The ferroelectric liquid crystal composition 2 prepared in Example 2 was paced in a cell of 2 μm in cell gap provided with transparent electrodes having the surfaces subjected to parallel aligning treatment by rubbing to prepare a liquid crystal cell, followed by placing this liquid crystal cell between two sheets of polarizers arranged in a crossed nicol prism state, and imparting a square wave of a low frequency (0.5 Hz and 20 V). As a result, a clear switching operation having a very good contrast (1:20) was observed, and a liquid crystal display element exhibiting a response time at 25° C. as very quick as 31 μsec was obtained.

Example 11

To the ferroelectric liquid crystal composition 2 prepared in Example 2 was added an anthraquinone dyestuff D-16 (prepared by BDH Co., Ltd.) expressed by the formula

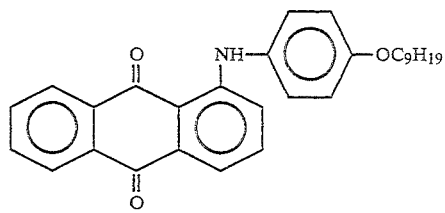

in 3% by weight to prepare a composition of guest host mode. This composition was filled in a cell of 8 μm in cell gap, subjected to the same treatment as in Example 9, followed by arranging a polarizer so that the polarization plane could be parallel to the molecular axis and impressing an alternating current of a low frequency of 0.5 Hz and 40 V. As a result, a clear switching operation having a very good contrast (1:10) was observed, and a liquid crystal display element having a response time as very quick as 85 μsec was obtained.

Example 12

A liquid crystal mixture 14 consisting of the following compounds was prepared:

| Compound A-1 | 27.3 wt. % |
|---|---|
| Compound A-3 | 7.8 wt. % |
| Compound A-4 | 15.6 wt. % |
| Compound A-31 | 15.6 wt. % |
| Compound A-34 | 11.7 wt. % |
| Compound B-3 | 12.0 wt. % |
| Compound C-1 | 10.0 wt. % |

This liquid crystal mixture 14 exhibited the following phase transition points:

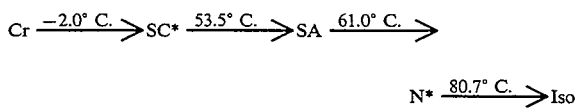

$Cr \xrightarrow{-2.0^\circ C.} SC^* \xrightarrow{53.5^\circ C.} SA \xrightarrow{61.0^\circ C.}$ $N^* \xrightarrow{80.7^\circ C.} Iso$ and also exhibited a Ps value of 25.3 nC/cm², a tilt angle of 23.2° and a response time of 57 μsec. The helical pitches in the SC* phase and N* phase of this mixture were 8 μm and 16 μm, respectively.

Example 13

A liquid crystal mixture 15 consisting of the following compounds was prepared:

| Compound A-4 | 11.7 wt. % |
|---|---|
| Compound A-5 | 15.6 wt. % |
| Compound A-20 | 19.5 wt. % |
| Compound A-21 | 15.6 wt. % |
| Compound A-22 | 15.6 wt. % |
| Compound B-3 | 12.0 wt. % |
| Compound C-2 | 10.0 wt. % |

This mixture exhibited the following phase transition points:

$Cr \xrightarrow{9.2^\circ C.} SC^* \xrightarrow{50.0^\circ C.} SA \xrightarrow{62.7^\circ C.} N^* \xrightarrow{71.0^\circ C.} Iso$ and its characteristic values at 25° C. were as follows: Ps: 35 nC/cm², tilt angle: 20°, response time: 40 μsec. Its helical pitch in the SC* phase was 7 μm and that in the N* phase at 63° C. was 15 μm.

Example 14

A liquid crystal mixture 16 consisting of the following compounds was prepared:

| Compound A-22 | 19.5 wt. % |
|---|---|
| Compound A-31 | 28.1 wt. % |
| Compound A-33 | 5.5 wt. % |
| Compound A-34 | 21.8 wt. % |
| Compound A-36 | 3.1 wt. % |
| Compound B-3 | 12.0 wt. % |
| Compound C-1 | 10.0 wt. % |

The mixture exhibited the following phase transition points:

$Cr \xrightarrow{-2.0^\circ C.} SC^* \xrightarrow{60.3^\circ C.} SA \xrightarrow{67.5^\circ C.}$ $N^* \xrightarrow{105.4^\circ C.} Iso$ The mixture exhibited a Ps value of 34.7 nC/cm², a tilt angle of 25.0° and a response time of 26 μsec, at 25° C.

Further, the helical pitch in the SC* phase was 7 μm and that in N* phase was 16 μm.

The liquid crystal mixture was filled in a cell prepared by providing transparent electrodes on a pair of glass substrates, followed by coating a polyimide film on the surface, rubbing it, and opposing the pair of glass substrates subjected to parallel aligning treatment to each other in a cell gap of 2 μm, gradually cooling the cell at a temperature-lowering rate of 1° C./min. starting from the state of isotropic liquid to prepare a liquid crystal element exhibiting SC* phase, placing this liquid crystal element between a pair of polarizers in a crossed nicol prism state and observing by means of a microscope. As a result, a uniform alignment having no fault was observed. Further, the contrast ratio of this liquid crystal element was 1:20.

Example 15

A base SC mixture IV consisting of the following 2 compounds of formula (A-I) and 3 compounds of formula (A-II) was prepared:

| Compound A-12 | 35 wt. % |
|---|---|
| Compound A-13 | 27 wt. % |
| Compound A-31 | 7 wt. % |
| Compound A-32 | 5 wt. % |
| Compound A-34 | 26 wt. % |

This base SC mixture IV exhibited the phase transition points:

$Cr \xrightarrow{9.0^\circ C.} SC \xrightarrow{55.3^\circ C.} SA \xrightarrow{95.7^\circ C.} N \xrightarrow{130.0^\circ C.} Iso$

Example 16

A base SC composition V consisting of the following one compound of the formula (A-I) and 4 compounds of the formula (A-II) was prepared:

| Compound A-14 | 40 wt. % |
|---|---|
| Compound A-31 | 29 wt. % |
| Compound A-33 | 5 wt. % |
| Compound A-34 | 23 wt. % |
| Compound A-36 | 3 wt. % |

The phase transition points of this base SC mixture V were as follows:

$Cr \xrightarrow{6.0^\circ C.} SC \xrightarrow{78^\circ C.} SA \xrightarrow{96.0^\circ C.} N \xrightarrow{103.7^\circ C.} Iso$

Example 17

A base SC mixture VI consisting of the following compounds was prepared in the same manner as in Example 16:

| Compound A-15 | 35 wt. % |
|---|---|
| Compound A-31 | 30 wt. % |

-continued

| | |
|---|---|
| Compound A-32 | 8 wt. % |
| Compound A-33 | 22 wt. % |
| Compound A-35 | 5 wt. % |

The phase transition points of this base SC mixture VI were as follows:

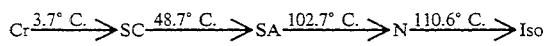

A ferroelectric liquid crystal mixture 17 consisting of the above base SC mixture VI, one optically active compound of the formula (B-III) and one optically active compound of the formula (C-VI) was prepared in the following proportions:

| | |
|---|---|
| Base SC mixture VI | 78 wt. % |
| Compound B-3 | 12 wt. % |
| Compound C-1 | 10 wt. % |

The phase transition points of this liquid crystal mixture 17 were as follows:

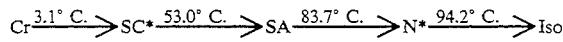

The characteristic values at 25° C. were as follows: Ps: 24.8 nC/cm$^2$, tilt angle: 17.8°, response time: 22 $\mu$sec, helical pitch in SC* phase: 9 $\mu$m, and helical pitch in N* phase: 15 $\mu$m.

Examples 18–25

Eight liquid crystal mixtures 18–25 shown in Tables 15–22 were prepared in the same manner as in Example 1. The characteristics of these mixtures were similarly measured. The results are shown in Table 23.

TABLE 15

| (Example 18) | |
|---|---|
| Compound A-16 | 12 wt. % |
| Compound A-18 | 5 wt. % |
| Compound A-19 | 10 wt. % |
| Compound A-31 | 15 wt. % |
| Compound A-33 | 15 wt. % |
| Compound A-34 | 15 wt. % |
| Compound A-36 | 10 wt. % |
| Compound B-1 | 2 wt. % |
| Compound B-2 | 8 wt. % |
| Compound C-1 | 4 wt. % |
| Compound C-2 | 2 wt. % |
| Compound C-6 | 2 wt. % |

TABLE 16

| (Example 19) | |
|---|---|
| Compound A-16 | 7 wt. % |
| Compound A-17 | 10 wt. % |
| Compound A-31 | 20 wt. % |
| Compound A-32 | 5 wt. % |
| Compound A-33 | 20 wt. % |
| Compound A-34 | 20 wt. % |
| Compound B-3 | 7 wt. % |
| Compound B-5 | 2 wt. % |
| Compound C-2 | 6 wt. % |
| Compound C-5 | 3 wt. % |

TABLE 17

| (Example 20) | |
|---|---|
| Compound A-16 | 4 wt. % |
| Compound A-17 | 4 wt. % |
| Compound A-19 | 10 wt. % |
| Compound A-33 | 12 wt. % |
| Compound A-34 | 20 wt. % |
| Compound A-36 | 20 wt. % |
| Compound B-1 | 7 wt. % |
| Compound B-6 | 3 wt. % |
| Compound B-9 | 6 wt. % |
| Compound C-1 | 7 wt. % |
| Compound C-6 | 3 wt. % |
| Compound C-7 | 4 wt. % |

TABLE 18

| (Example 21) | |
|---|---|
| Compound A-16 | 15 wt. % |
| Compound A-17 | 14 wt. % |
| Compound A-18 | 7 wt. % |
| Compound A-31 | 6 wt. % |
| Compound A-32 | 15 wt. % |
| Compound A-33 | 6 wt. % |
| Compound A-36 | 25 wt. % |
| Compound B-5 | 3 wt. % |
| Compound B-9 | 2 wt. % |
| Compound C-2 | 3 wt. % |
| Compound C-6 | 2 wt. % |
| Compound C-7 | 2 wt. % |

TABLE 19

| (Example 22) | |
|---|---|
| Compound A-17 | 10 wt. % |
| Compound A-19 | 13 wt. % |
| Compound A-31 | 10 wt. % |
| Compound A-33 | 12 wt. % |
| Compound A-34 | 12 wt. % |
| Compound A-36 | 20 wt. % |
| Compound B-3 | 5 wt. % |
| Compound B-5 | 3 wt. % |
| Compound B-8 | 4 wt. % |
| Compound C-1 | 5 wt. % |
| Compound C-2 | 3 wt. % |
| Compound C-5 | 3 wt. % |

TABLE 20

| (Example 23) | |
|---|---|
| Compound A-17 | 15 wt. % |
| Compound A-18 | 2 wt. % |
| Compound A-19 | 12 wt. % |
| Compound A-31 | 20 wt. % |
| Compound A-32 | 4 wt. % |
| Compound A-33 | 15 wt. % |
| Compound A-36 | 15 wt. % |
| Compound B-3 | 4 wt. % |
| Compound B-6 | 3 wt. % |
| Compound C-5 | 5 wt. % |
| Compound C-6 | 2 wt. % |
| Compound C-7 | 3 wt. % |

TABLE 21

| (Example 24) | |
|---|---|
| Compound A-16 | 10 wt. % |
| Compound A-17 | 10 wt. % |
| Compound A-19 | 10 wt. % |
| Compound A-31 | 10 wt. % |
| Compound A-33 | 15 wt. % |
| Compound A-34 | 15 wt. % |
| Compound A-36 | 5 wt. % |
| Compound B-2 | 4 wt. % |
| Compound B-6 | 4 wt. % |
| Compound B-7 | 3 wt. % |
| Compound B-9 | 2 wt. % |

TABLE 21-continued (Example 24)

| Compound C-1 | 4 wt. % |
|---|---|
| Compound C-5 | 3 wt. % |
| Compound C-7 | 5 wt. % |

TABLE 22

(Example 25)

| Compound A-16 | 8 wt. % |
|---|---|
| Compound A-17 | 8 wt. % |
| Compound A-19 | 15 wt. % |
| Compound A-31 | 25 wt. % |
| Compound A-32 | 3 wt. % |
| Compound A-33 | 20 wt. % |
| Compound A-36 | 5 wt. % |
| Compound B-2 | 2 wt. % |
| Compound B-3 | 2 wt. % |
| Compound B-7 | 2 wt. % |
| Compound B-8 | 2 wt. % |
| Compound C-1 | 2 wt. % |
| Compound C-2 | 2 wt. % |
| Compound C-7 | 4 wt. % |

TABLE 23

| | Phase transition point (°C.) | | | | Spontaneous polarization nC/cm² | Tilt angle (°) | Helical pitch (μm) | | Response time (μsec) |
|---|---|---|---|---|---|---|---|---|---|
| | Cr → SC* | SC* → SA | SA → N* | N* → Iso | | | SC* phase | N* phase | |
| Example 18 | −7 | 62 | 83 | 100 | 26 | 23 | 7 | 16 | 27 |
| Example 19 | −10 | 68 | 84 | 106 | 27 | 22 | 8 | 20 | 26 |
| Example 20 | −8 | 67 | 88 | 109 | 35 | 19 | 10 | 10 | 20 |
| Example 21 | −9 | 55 | 83 | 93 | 18 | 24 | 12 | 30 | 27 |
| Example 22 | −8 | 63 | 87 | 103 | 29 | 22 | 8 | 27 | 25 |
| Example 23 | −7 | 59 | 86 | 104 | 21 | 23 | 10 | 25 | 29 |
| Example 24 | −6 | 56 | 80 | 100 | 26 | 18 | 7 | 12 | 19 |
| Example 25 | −7 | 57 | 81 | 93 | 20 | 22 | 9 | 26 | 23 |

Examples 26–28

A smectic C mixture T consisting of the following 4 biphenylyl compounds was prepared, followed by using this smectic C mixture T to prepare base SC mixtures VII, VIII and IX having compositions shown in Tables 23, 24 and 25, respectively:

| Base smectic C mixture T | |
|---|---|
| Compound A-31 | 38 wt. % |
| Compound A-33 | 10 wt. % |
| Compound A-34 | 48 wt. % |
| Compound A-36 | 4 wt. % |

TABLE 23

| Compound A-1 | 30 wt. % |
|---|---|
| Compound A-3 | 8 wt. % |
| Compound A-4 | 12 wt. % |
| Base SC mixture T | 50 wt. % |

TABLE 24

| Compound A-6 | 27 wt. % |
|---|---|
| Compound A-7 | 11 wt. % |
| Compound A-10 | 12 wt. % |
| Base SC mixture T | 50 wt. % |

TABLE 25

| Compound A-23 | 18 wt. % |
|---|---|
| Compound A-24 | 12 wt. % |
| Compound A-17 | 20 wt. % |
| Base SC mixture T | 50 wt. % |

The phase transition points of base SC mixtures VII, VIII and IX are shown in Table 26.

Using these base SC mixtures, ferroelectric liquid crystal mixtures 26–28 having compositions shown in Tables 23-1, 24-1 and 25-1, respectively were prepared.

TABLE 23-1

(Example 26)

| Base SC mixture VII | 78 wt. % |
|---|---|
| Compound B-3 | 12 wt. % |
| Compound C-2 | 10 wt. % |

TABLE 25-1

(Example 28)

| Base SC mixture IX | 78 wt. % |
|---|---|
| Compound B-3 | 12 wt. % |
| Compound C-2 | 10 wt. % |

TABLE 24-1

(Example 27)

| Base SC mixture VIII | 78 wt. % |
|---|---|
| Compound B-3 | 12 wt. % |
| Compound C-2 | 10 wt. % |

The phase transition points and the characteristic values of the ferroelectric mixtures 26–28 are shown in Table 26.

TABLE 26

| | Phase transition points (°C) | | | | Spontaneous polarization nC/cm² | Tilt angle (°) | Response time (μsec) |
|---|---|---|---|---|---|---|---|
| | Cr → SC* | SC* → SA | SA → N* | N* → Iso | | | |
| Mixture VII | 8 | 71 | 75 | 106 | — | — | — |
| Mixture VIII | 19 | 73 | 106 | 110 | — | — | — |
| Mixture IX | −1 | 47 | 99 | 102 | — | — | — |
| Example 26 | −11 | 59 | 61 | 91 | 34 | 27 | 41 |
| Example 27 | −8 | 55 | 87 | 94 | 33 | 20 | 30 |
| Example 28 | −12 | 50 | 80 | 86 | 19 | 17 | 16 |

Example 29

A base SC mixture X having the following composition was prepared:

| Compound A-24 | 35 wt. % |
|---|---|
| Compound A-31 | 25 wt. % |
| Compound A-33 | 6 wt. % |
| Compound A-34 | 31 wt. % |
| Compound A-36 | 3 wt. % |

The phase transition points (°C.) of this mixture X were as follows:
Cr 2 SC 61 SA 105 N 114 Iso Using this mixture X, a ferroelectric mixture 29 having the following composition was prepared:

| Mixture X | 78 wt. % |
|---|---|
| Compound B-3 | 12 wt. % |
| Compound C-2 | 10 wt. % |

The phase transition points (°C.) and the characteristic values of this mixture 29 are shown below.
Cr -12 SC* 61 SA 85 N* 97 Iso
 Spontaneous polarization: 28 nC/cm$^2$
 Tilt angle: 19°
 Response time: 26 μsec
 Helical pitch in SC* phase: 3 μm
 Helical pitch in N* phase: 37 μm (Effectiveness of the Invention)

By combining liquid crystal compounds together as in the present invention, a ferroelectric liquid crystal composition having high speed response properties and exhibiting the SC* phase within a broad temperature range including room temperature is obtained.

Further, the light-switching element using the liquid crystal composition of the present invention effects a clear switching operation in either a birefringence display mode or a guest host display mode; hence the element is a liquid crystal display element having a very quick response rate.

What is claimed is:

1. A ferroelectric smectic C liquid crystal composition comprising the following three components A, B and C, the mixing proportions of component A, component B and component C being 55 to 91% by weight, 5 to 25% by weight and 4 to 20% by weight, respectively, based upon the total quantity of the three components:

the component A is being at least one compound selected from among compounds expressed by the formula

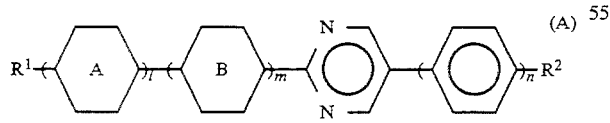

wherein

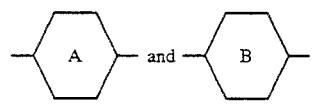

and each independently represent

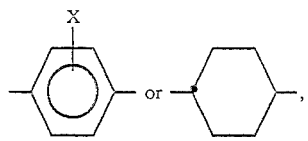

$R^1$ and $R^2$ each represent the same or different linear or branched alkyl group, alkoxy group or alkanoyloxy group each of 1 to 18 carbon atoms, X represents a hydrogen atom, a halogen atom or a cyano group, l, m and n each represent an integer of 0 or 1 and (l+m+n) is 1 or 2, and having a smectic C phase;

the component B being at least one compound selected from among optically active compounds expressed by the formula

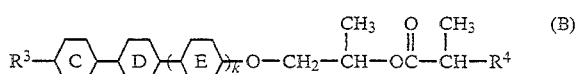

wherein

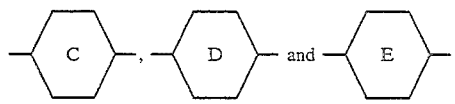

each independently

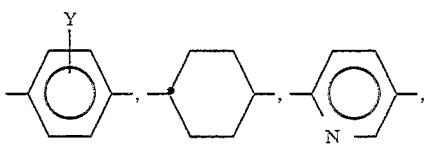

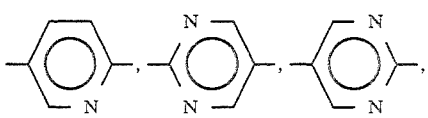

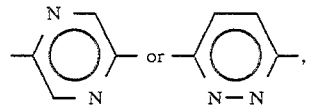

Y represents a hydrogen atom, a halogen atom or cyano group, k represents an integer of 0 or 1, $R^3$ represents a linear or branched alkyl group or alkoxy group each of 1 to 18 carbon atoms, $R^4$ represents an alkyl group of 2 to 18 carbon atoms or a linear or branched alkoxy group of 1 to 18 carbon atoms and the symbol * represents an asymmetric carbon atom, the above-mentioned optically active compounds having to one another the same sense of the spontaneous polarization in a chiral smectic C phase induced when dissolved in a smectic C liquid crystal; and the component C being at least one compound selected from among optically active compounds expressed by the formula

wherein

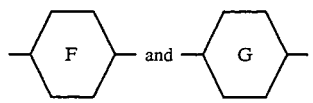

each independently represent

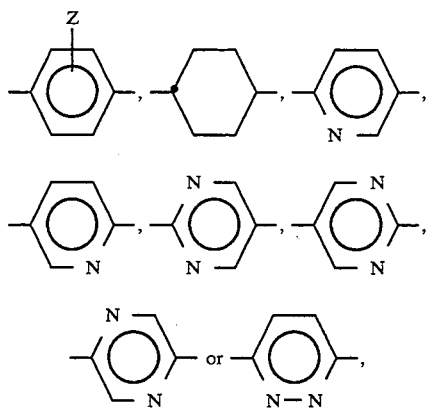

Z represents a hydrogen atom, a halogen atom or cyano group, $R^5$ and $R^6$ each represent the same or different linear or branched alkyl group or alkoxy group each of 1 to 18 carbon atoms and the symbol * represents an asymmetric carbon atom, the above-mentioned optically active compounds having the same sense of the spontaneous polarization in a chiral smectic C phase induced when dissolved in a smectic C liquid crystal, as the sense of the compounds of the component B.

2. A ferroelectric smectic C liquid crystal composition according to claim 1, wherein component A is at least one compound selected from compounds expressed by the formula

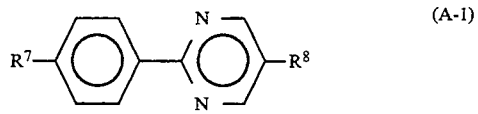

wherein $R^7$ and $R^8$ each represent the same or different, linear or branched alkyl group, alkoxy group or alkanoyloxy group each of 1 to 18 carbon atoms, or the formula

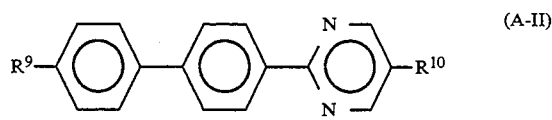

wherein $R^9$ and $R^{10}$ each represent the same or different, linear or branched alkyl group or alkoxy group each of 1 to 18 carbon atoms, the above-mentioned compounds having a smectic C phase.

3. A ferroelectric smectic C liquid crystal composition according to claim 1, wherein component B is at least one Compound selected from among optically active compounds expressed by either one of the following three formulas, the above-mentioned optically active compounds having to one another, the same sense of the spontaneous polarizations in a chiral smectic C phase induced when dissolved in smectic C liquid crystal;

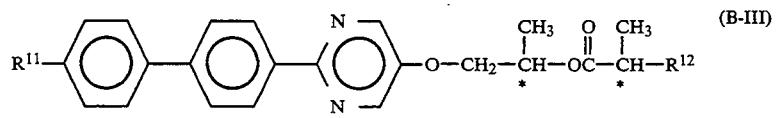

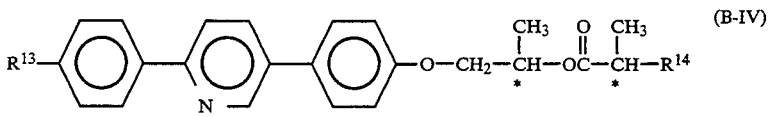

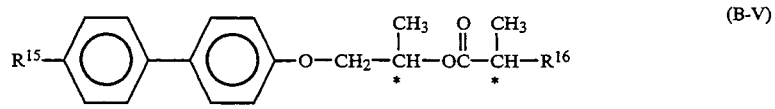

wherein $R^{11}$, $R^{13}$ and $R^{15}$ each independently represent a linear or branched alkyl group or alkoxy group each of 1 to 18 carbon atoms, , $R^{12}$, $R^{14}$ and $R^{16}$ each independently represent a linear or branched alkyl group of 2 to 18 carbon atoms or a linear or branched alkoxy group of 1 to 18 carbon atoms and the symbol * represents an asymmetric carbon atom.

4. A ferroelectric smectic C liquid crystal composition according to claim 1, wherein component C is at least one compound selected from among optically active compounds expressed by the formula

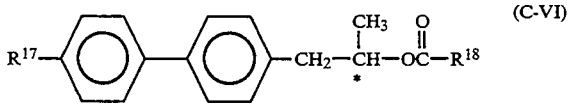

wherein $R^{17}$ and $R^{18}$ each independently represent a linear or branched alkyl group or alkoxy group each of 1 to 18 carbon atoms and the symbol * represents an asymmetric carbon atom, the above-mentioned optically active compounds having the same sense of the spontaneous polarization in a chiral smectic C phase induced when dissolved in smectic C liquid crystal, as the sense of the compound of the component B.

5. A ferroelectric smectic C liquid crystal composition according to claim 1, wherein component A is at least one compound selected from among compounds expressed by the formula

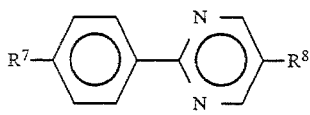
(A-I')

wherein $R^7$ represents a linear alkyl group, alkoxy group or alkanoyloxy group each of 5 to 14 carbon atoms and $R^8$ represents a linear alkyl group or alkoxy group each of 4 to 16 carbon atoms, or the formula

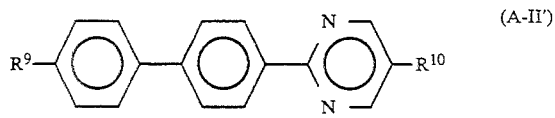
(A-II')

wherein $R^9$ and $R^{10}$ each independently represent a linear alkyl group or alkoxy group each of 5 to 10 carbon atoms, and having a smectic C phase.

6. A ferroelectric smectic C liquid crystal composition according to claim 1, wherein component A is at least one compound selected from among compounds expressed by the formula

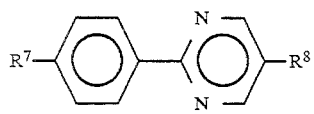
(A-I'')

wherein $R^7$ represents a linear alkyl group or alkoxy group each of 6 to 12 carbon atoms and $R^8$ represents a linear alkoxy group of 6 to 15 carbon atoms, or the formula

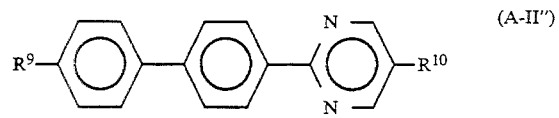
(A-II'')

wherein $R^9$ represents a linear alkyl group or alkoxy group each of 5 to 8 carbon atoms and $R^{10}$ represents a linear alkyl group of 6 to 8 carbon atoms, and having a smectic C phase.

7. A ferroelectric smectic C liquid crystal composition according to claim 1, wherein component A is at least one compound selected from among compounds expressed by the formula

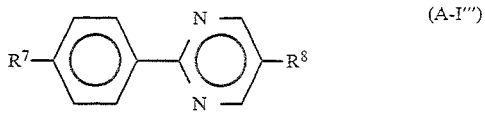
(A-I''')

wherein $R^7$ represents an alkyl group of 7 to 14 carbon atoms and $R^8$ represents an alkyl group of 10 to 14 carbon atoms, or the formula

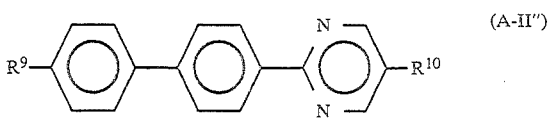
(A-II''')

wherein $R^9$ represents a linear alkyl group or alkoxy group each of 5 to 8 carbon atoms and $R^{10}$ represents a linear alkyl group of 6 to 8 carbon atoms, and having a smectic C phase.

8. A ferroelectric smectic C liquid crystal composition according to claim 1, wherein component B is at least one compound selected from among optically active compounds expressed by either one of the following three formulas,
the above-mentioned optically active compounds having to one another the same sense of the spontaneous polarization in a chiral smectic C phase induced when dissolved in smectic C liquid crystal;

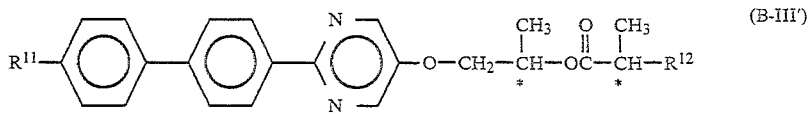
(B-III')

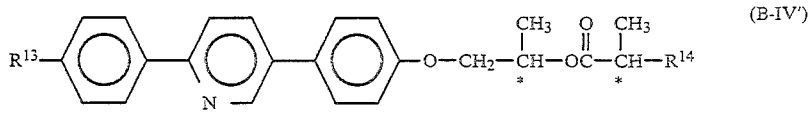
(B-IV')

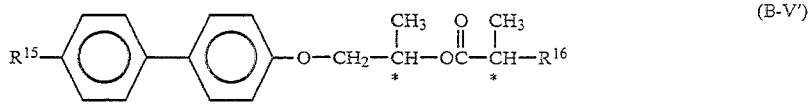
(B-V')

wherein $R^{11}$ and $R^{13}$ each independently represent a linear alkyl group or alkoxy group each of 3 to 10 carbon atoms, $R^{15}$ represents a linear alkyl group or alkoxy group each of 3 to 12 carbon atoms, $R^{12}$, $R^{14}$ and $R^{16}$ each independently represent a linear alkyl group or alkoxy group each of 2 to 10 carbon atoms and the symbol * represents an asymmetric carbon atom.

9. A ferroelectric smectic C Liquid crystal composition according to claim 1, wherein component C is at least one compound selected from among compounds expressed by the formula

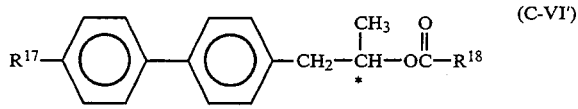

wherein $R^{17}$ represents a linear alkoxy group of 3 to 10 carbon atoms, $R^{18}$ represents an alkyl group of 2 to 6 carbon atoms and the symbol * represents an asymmetric carbon atom, the above-mentioned optically active compounds having the same sense of the spontaneous polarization in a chiral smectic C phase induced when dissolved in smectic C liquid crystal, as the sense of the compound of the component B.

10. A ferroelectric smectic C liquid crystal composition according to claim 1, wherein component A is a smectic C liquid crystal mixture consisting of

| | |
|---|---|
| 2-(4-octylphenyl)-5-undecylpyrimidine | 35% by weight, |
| 2-(4-pentylbiphenyl-4'-yl)-5-hexylpyrimidine | 25% by weight, |
| 2-(4-hexylbiphenyl-4'-yl)-5-hexylpyrimidine | 6% by weight, |
| 2-(4-heptylbiphenyl-4'-yl)-5-hexylpyrimidine and | 31% by weight, |
| 2-(4-octylbiphenyl-4'-yl)-5-hexylpyrimidine | 3% by weight. |

11. A ferroelectric smectic C liquid crystal composition according to claim 1, wherein component B is a compound expressed by the formula

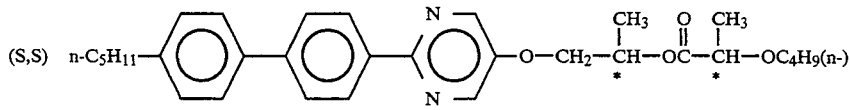

and the component C is a compound expressed by the formula

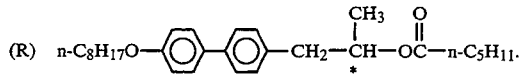

12. A light-switching element containing a ferroelectric smectic C liquid crystal composition as set forth in claim 1.
13. A light-switching element containing a ferroelectric smectic C liquid crystal composition as set forth in claim 2.
14. A light-switching element containing a ferroelectric smectic C liquid crystal composition as set forth in claim 3.
15. A light-switching element containing a ferroelectric smectic C liquid crystal composition as set forth in claim 4.
16. A light-switching element containing a ferroelectric smectic C liquid crystal composition as set forth in claim 5.
17. A light-switching element containing a ferroelectric smectic C liquid crystal composition as set forth in claim 6.
18. A light-switching element containing a ferroelectric smectic C liquid crystal composition as set forth in claim 7.
19. A light-switching element containing a ferroelectric smectic C liquid crystal composition as set forth in claim 8.
20. A light-switching element containing a ferroelectric smectic C liquid crystal composition as set forth in claim 9.
21. A light-switching element containing a ferroelectric smectic C liquid crystal composition as set forth in claim 10.
22. A light-switching element containing a ferroelectric smectic C liquid crystal composition as set forth in claim 11.
23. A ferroelectric smectic C liquid crystal composition according to claim 1 wherein components B and C have opposite helical twist senses with respect to each other.
24. A light-switching element according to claim 12 wherein components B and C have opposite helical twist senses with respect to each other.

* * * * *

UNITED STATES PATENT AND TRADEMARK OFFICE
CERTIFICATE OF CORRECTION

PATENT NO. : 5,427,714
DATED : June 27, 1995
INVENTOR(S) : Murashiro et al.

It is certified that error appears in the above-indentified patent and that said Letters Patent is hereby corrected as shown below:

On the title page: Item [56]
In References Cited, Column 2, Line 1, change "2659864" to --265986--;

Column 33, Line 51, delete "is";

Last line, delete "and";

Column 34, Line 34, after "independently" insert --represent --.

Signed and Sealed this

Ninth Day of January, 1996

Attest:

BRUCE LEHMAN

Attesting Officer

Commissioner of Patents and Trademarks